(12) United States Patent
Robinson et al.

(10) Patent No.: US 12,324,728 B2
(45) Date of Patent: Jun. 10, 2025

(54) MANIFOLDING APPARATUS OR DRESSING EXHIBITING LOW TISSUE INGROWTH AND NEGATIVE-PRESSURE TREATMENT METHOD

(71) Applicant: Solventum Intellectual Properties Company, Maplewood, MN (US)

(72) Inventors: Timothy Mark Robinson, Shillingstone (GB); Christopher Brian Locke, Bournemouth (GB); Benjamin Andrew Pratt, Poole (GB); Larry Tab Randolph, San Antonio, TX (US); Justin Alexander Long, Lago Vista, TX (US); James Courage, San Antonio, TX (US); Diwi L. Allen, San Antonio, TX (US); Kristine M. Kieswetter, San Antonio, TX (US)

(73) Assignee: Solventum Intellectual Properties Company, Maplewood, MN (US)

( * ) Notice: Subject to any disclaimer, the term of this patent is extended or adjusted under 35 U.S.C. 154(b) by 507 days.

(21) Appl. No.: 17/861,074

(22) Filed: Jul. 8, 2022

(65) Prior Publication Data
US 2022/0347017 A1    Nov. 3, 2022

Related U.S. Application Data

(63) Continuation of application No. 16/757,343, filed as application No. PCT/US2018/056831 on Oct. 22, 2018, now abandoned.
(Continued)

(51) Int. Cl.
*A61F 13/05* (2024.01)
*A61F 13/01* (2024.01)
(Continued)

(52) U.S. Cl.
CPC ........ *A61F 13/05* (2024.01); *A61F 13/01021* (2024.01); *A61F 13/0206* (2013.01);
(Continued)

(58) Field of Classification Search
CPC .............. A61F 13/148; A61F 13/00021; A61F 13/0216; A61F 2013/00157;
(Continued)

(56) References Cited

U.S. PATENT DOCUMENTS 1,355,846 A    10/1920    Rannells
2,547,758 A     4/1951    Keeling
(Continued)

FOREIGN PATENT DOCUMENTS

AU    550575 B2    3/1986
AU    745271 B2    3/2002
(Continued)

OTHER PUBLICATIONS

International Search Report and Written Opinion for Corresponding Application No. PCT/US2018/056831, mailed Feb. 18, 2019.
(Continued)

*Primary Examiner* — Susan S Su

(57) ABSTRACT

An apparatus for filling a wound can include an array of at least four truncated ellipsoids interconnected to define at least one fluid path through, for example perpendicular to, the array. The longest principal axis of each ellipsoid may be perpendicular to the array. Each truncated ellipsoid may be a spheroid and/or may include an approximately elliptical contact surface at each contact surface between two interconnected ellipsoids. Each fluid pathway may have four continuously-curved concave sides and may have a parallelogram-shaped cross-section with continuously-curved concave edges. A dressing may include the apparatus, a dressing layer coupled to the apparatus, a backing layer
(Continued)

FIG. 1F disposed over a surface of the dressing layer opposite the apparatus, and an attachment device disposed on at least a margin of the backing layer. Methods of treating various tissue sites using the apparatus or dressing with negative-pressure therapy are also disclosed.

17 Claims, 6 Drawing Sheets

Related U.S. Application Data

(60) Provisional application No. 62/577,570, filed on Oct. 26, 2017.

(51) Int. Cl.
*A61F 13/0206* (2024.01)
*A61F 13/14* (2006.01)
*A61L 27/16* (2006.01)
*A61L 27/18* (2006.01)
*A61L 27/34* (2006.01)
*A61L 27/54* (2006.01)
*A61M 1/00* (2006.01)
*A61F 13/00* (2006.01)

(52) U.S. Cl.
CPC ............ *A61F 13/148* (2013.01); *A61L 27/16* (2013.01); *A61L 27/18* (2013.01); *A61L 27/34* (2013.01); *A61L 27/54* (2013.01); *A61M 1/85* (2021.05); *A61M 1/90* (2021.05); *A61M 1/915* (2021.05); *A61F 2013/00157* (2013.01); *A61F 2013/00357* (2013.01); *A61M 1/92* (2021.05); *A61M 2210/1017* (2013.01); *A61M 2210/1021* (2013.01)

(58) Field of Classification Search
CPC .... A61F 2013/00357; A61F 13/00068; A61M 1/85; A61M 1/90; A61L 27/16; A61L 27/18; A61L 27/37; A61L 27/54
See application file for complete search history.

(56) References Cited

U.S. PATENT DOCUMENTS

| | | | |
|---|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |

(56) References Cited

U.S. PATENT DOCUMENTS

| | | | |
|---|---|---|---|
| 8,568,386 | B2 | 10/2013 | Malhi |
| 8,679,081 | B2 | 3/2014 | Heagle et al. |
| 8,834,451 | B2 | 9/2014 | Blott et al. |
| 8,926,592 | B2 | 1/2015 | Blott et al. |
| 9,017,302 | B2 | 4/2015 | Vitaris et al. |
| 9,198,801 | B2 | 12/2015 | Weston |
| 9,211,365 | B2 | 12/2015 | Weston |
| 9,289,542 | B2 | 3/2016 | Blott et al. |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2007/0185463 | A1 | 8/2007 | Mulligan |
| 2014/0163491 | A1 | 6/2014 | Schuessler et al. |
| 2015/0080788 | A1 | 3/2015 | Blott et al. |
| 2016/0166744 | A1* | 6/2016 | Hartwell ............... A61M 1/916 604/319 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 2367578 A2 | 9/2011 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 2008104609 A1 | 9/2008 |
| WO | 2017119996 A1 | 7/2017 |
| WO | 2018226624 A1 | 12/2018 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., JR., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ? uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

(56) References Cited

OTHER PUBLICATIONS

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, the Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

* cited by examiner

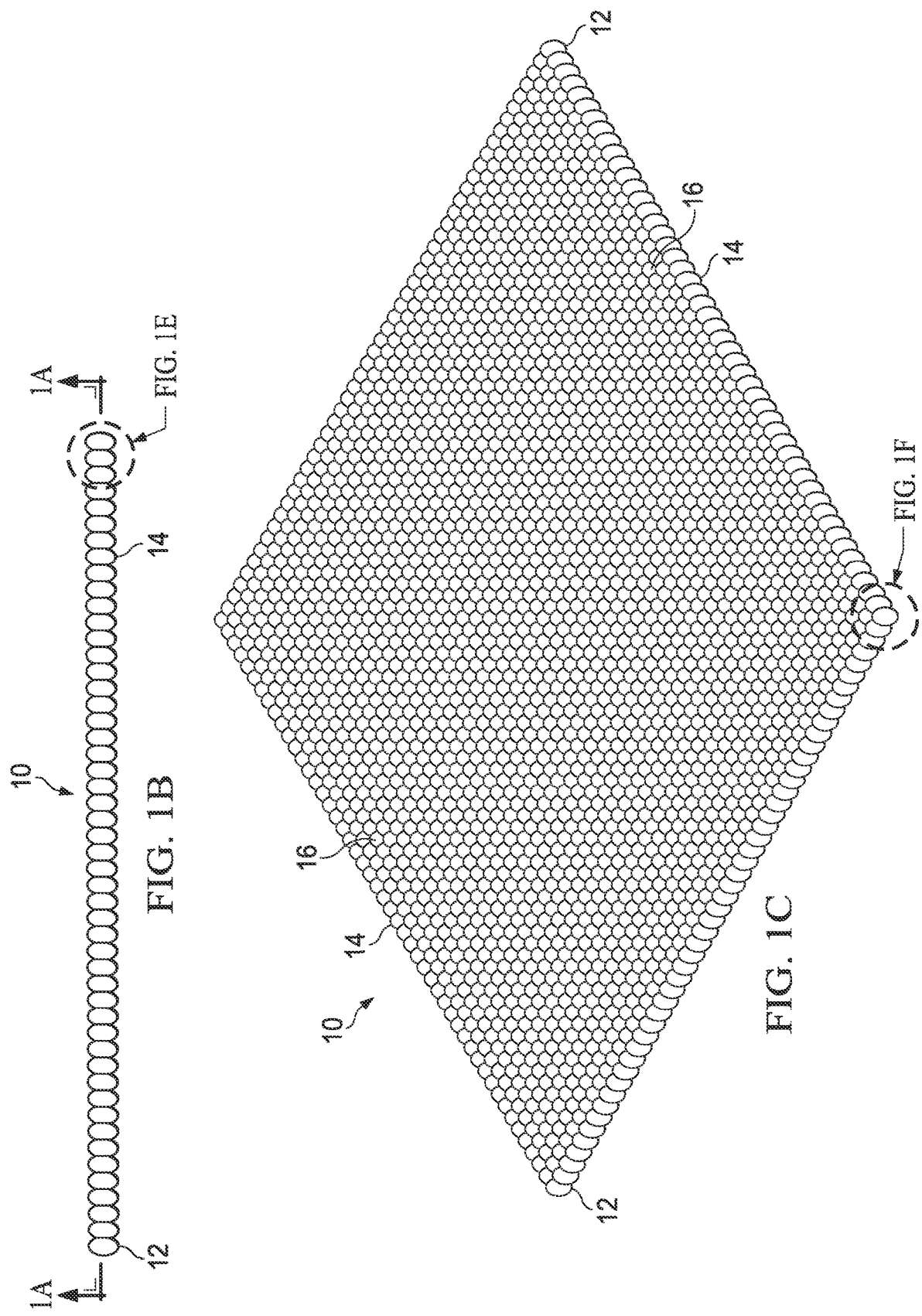

MANIFOLDING APPARATUS OR DRESSING EXHIBITING LOW TISSUE INGROWTH AND NEGATIVE-PRESSURE TREATMENT METHOD

RELATED APPLICATIONS

This application is a Continuation of U.S. patent application Ser. No. 16/757,343, filed Apr. 17, 2020, which is a U.S. National Stage Entry of PCT/US2018/056831, filed Oct. 22, 2018, which claims the benefit, under 35 USC 119(e), of the filing of U.S. Provisional Patent Application Ser. No. 62/577,570, entitled "Manifolding Apparatus or Dressing Exhibiting Low Tissue Ingrowth and Negative-Pressure Treatment Method", filed Oct. 26, 2017, all of which are incorporated herein by reference in their entirety.

TECHNICAL FIELD

The invention set forth in the appended claims relates generally to tissue treatment systems optionally with negative pressure and/or instillation and more particularly, but without limitation, to compartmented site treatment systems that may exhibit relatively low levels of tissue ingrowth.

BACKGROUND

A wide variety of materials and devices, generally characterized as "dressings" or "wound dressings," are generally known in the art for use in treating an injury or other disruption of tissue. Such wounds or tissue sites may be the result of trauma, surgery, or disease, and may affect skin or other tissues. In general, dressings may control bleeding, absorb wound exudate, ease pain, assist in debriding the wound, protect tissue site from infection, or otherwise promote healing and protect the tissue site from further damage.

Although the clinical benefits and advantages of dressings may be widely accepted, improvements to dressings may benefit healthcare providers and patients.

Clinical studies and practice have also shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood and interstitial fluid flow, and micro-deformation of tissue at a wound site. Together, these benefits can increase development of granulation tissue and reduce healing times.

There is also widespread acceptance that cleansing a tissue site can be highly beneficial for new tissue growth. For example, a wound can be washed out with a stream of liquid solution, or a cavity can be washed out using a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a tissue site can be combined with negative-pressure therapy to further promote tissue healing by loosening soluble contaminants at a tissue site and removing infectious material. As a result, soluble bacterial burden can be decreased, contaminants removed, and the tissue site cleansed.

While the clinical benefits of negative-pressure therapy and/or instillation therapy are widely known, improvements to therapy systems, components such as dressings, and processes may benefit healthcare providers and patients.

BRIEF SUMMARY

New and useful compositions of tissue site filler layers, dressing layers, and dressings including such tissue site filler or dressing layers, methods for manufacturing same, systems including same, apparatuses including same, and methods for treating a tissue site, for example in a negative-pressure therapy environment, are set forth in the following summary and description, as well as in the appended claims. Illustrative embodiments are also provided to enable a person skilled in the art to make and use the claimed subject matter.

For example, in some embodiments, an apparatus for filling a wound can include an array of at least four truncated ellipsoids interconnected to define at least one fluid path through the array. In some embodiments, the interconnected ellipsoids may be comprised of a polyolefin, a polyester, a polyamide, a polystyrene, a polydiolefin, a polyacrylonitrile, a polysiloxane, or a copolymer or combination thereof. In some embodiments, each of the interconnected ellipsoids may have a surface hardness from about 0 Shore A to about 25 Shore A.

In some example embodiments, an apparatus for filling a wound can include an array of interconnected polymeric ovules having a truncated ellipsoidal shape. In some embodiments, each set of four interconnected ovules in the array may define a fluid pathway extending perpendicularly through the array, and each truncated ellipsoidal shape may comprise an approximately elliptical contact surface at each contact surface between two interconnected ovules. In some embodiments, each interconnected polymeric ovule may have its longest principal axis oriented substantially perpendicular to the array.

In some example embodiments, an apparatus for filling a wound can include a layer having a plurality of fluid pathways through the layer from a first surface to a second surface. In some embodiments, an array of connected polymeric protrusions may extend through the layer connecting the first and second surfaces. In some embodiments, each set of four connected polymeric protrusions from each of the first and second surfaces of the array may define one fluid pathway extending perpendicularly through the array. In some embodiments, each fluid pathway may have four continuously-curved concave sides and may have a parallelogram-shaped cross-section with continuously-curved concave edges.

In some example embodiments, a dressing for treating a tissue site may include an apparatus for filling a wound, a dressing layer coupled to the apparatus, a backing layer disposed over a surface of the dressing layer opposite from the apparatus, and an attachment device disposed on at least a margin of the backing layer. In some embodiments, the dressing layer may include or be a manifolding layer configured to allow both fluid removal and fluid instillation therethrough. In some embodiments, the dressing layer and the apparatus may be coupled together and the apparatus may be configured to allow fluid removal. In some embodiments, the attachment device may be configured to form a seal with a tissue site. In some embodiments, the dressing layer may be coupled to the apparatus on a surface opposite the protrusions, or on a surface formed by truncation of the ovules or of the ellipsoids on one end of a principal axis oriented substantially perpendicular to the array.

In some example embodiments, a system for treating a tissue site with negative pressure may include: an apparatus or a dressing for treating a tissue site, as described above or herein; and a negative-pressure source fluidly coupled to the dressing and configured to enable fluid removal through the dressing. In some embodiments the system may further include: a negative-pressure conduit; and a negative-pressure connector subsystem for fluidly coupling the negative-pressure source to the apparatus or to the dressing for fluid removal.

In some embodiments, a method for treating a compartmented tissue site, such as an overhang wound or a peritoneal or abdominal cavity, may include: deploying within the compartmented tissue site an apparatus, a dressing, or at least a portion of a system for treating a tissue site; and deploying a sealing member to form a fluid seal over an open cavity. In some embodiments, the method may additionally include deploying a negative-pressure connector subsystem; fluidly coupling the negative-pressure connector subsystem to a negative-pressure source; and activating the negative-pressure source.

In some embodiments, a method for treating a surface tissue site, such as a burn, a graft, or a post-operative wound, may include: deploying over the surface tissue site an apparatus, a dressing, or at least a portion of a system for treating a tissue site; and deploying a sealing member to form a fluid seal over the surface tissue site. In some embodiments, the method may additionally include deploying a negative-pressure connector subsystem; fluidly coupling the negative-pressure connector subsystem to a negative-pressure source; and activating the negative-pressure source.

In some embodiments, a method for treating a tunnel wound site, such as a puncture or a fistula, may include: deploying within the tunnel wound site an apparatus, a dressing, or at least a portion of a system for treating a tissue site; and deploying a sealing member to form a fluid seal over the tunnel wound site. In some tunnel wound site embodiments, the substrate of the dressing or system may comprise a cylinder or tube. In some embodiments, the method may additionally include deploying a negative-pressure connector subsystem; fluidly coupling the negative-pressure connector subsystem to a negative-pressure source; and activating the negative-pressure source.

In some embodiments, a method of reducing edema and/or increasing interstitial fluid flow for a tissue site may include positioning an apparatus, a dressing, or at least a portion of a system for treating a tissue site over the tissue site.

Objectives, advantages, and a preferred mode of making and using the claimed subject matter may be understood best by reference to the accompanying drawings in conjunction with the following detailed description of illustrative embodiments.

BRIEF DESCRIPTION OF THE DRAWINGS

FIGS. 1A-1C are perspective views of a wound filler sheet useful for treating a tissue site. FIG. 1A is a top view; FIG. 1B is a side view; and FIG. 1C is a perspective view.

DESCRIPTION OF EXAMPLE EMBODIMENTS

Figure 1A:
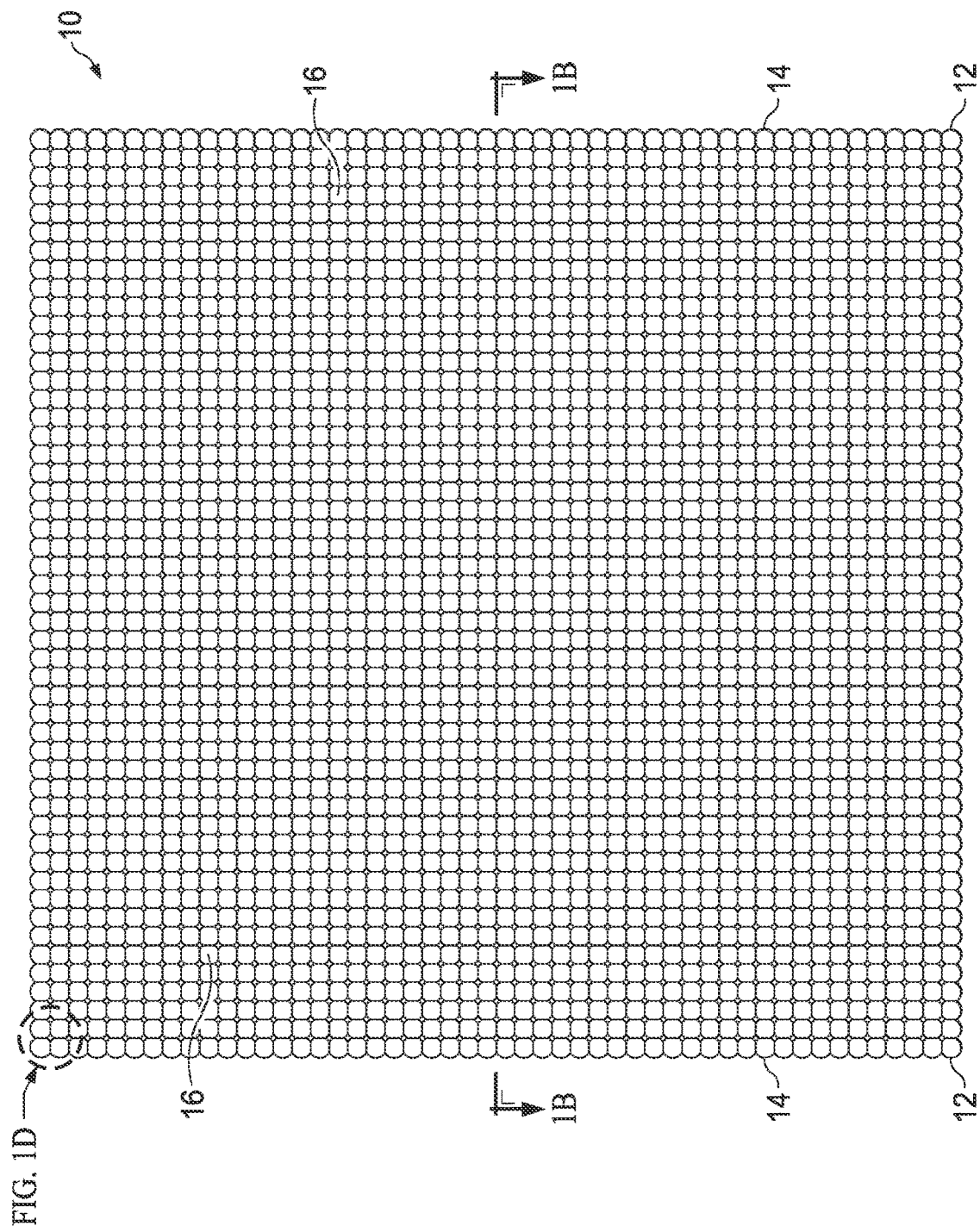

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Disclosed herein are embodiments of a wound filler, a dressing layer containing a such a wound filler, embodiments of composite dressings including such a dressing layer, and embodiments of therapy systems including same. Also disclosed herein are embodiments of related methods, such as methods of making and methods of using the disclosed wound fillers, dressing layers, composite dressings, and therapy systems. For example, FIG. 1 illustrates an embodiment of a dressing 100. Generally, and as will be disclosed herein, the dressing 100 may be configured to provide therapy to a tissue site in accordance with the disclosure of this specification.

The term "tissue site" in this context broadly refers to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. Compartmented tissue may include a wound, defect, or other treatment target in a body cavity, such as an abdominal cavity, for example. The term "tissue site" may also refer to areas of any tissue that are not necessarily wounded or defective, for example with respect to pressure ulcer prevention, but are instead areas in which it may be desirable to add or promote the growth of additional tissue. For example, negative pressure may be applied to a tissue site to grow additional tissue that may be harvested and transplanted.

In some embodiments, treatment of a tissue site can include a wound filler layer configured to interface with the tissue site. For example, in the embodiment of FIGS. 1A-1F, the wound filler 10 an array of interconnected ovules having a truncated ellipsoidal shape. With respect to wound fillers, such as wound filler 10, and dressing layers made of wound filler material, the terms "ovules" and "ellipsoids" are used interchangeably herein, often adjectivally modified by "truncated," to refer to individual shaped portions interconnected in array form.

FIG. 1A shows a top view of wound filler 10; FIG. 1B shows a side view of wound filler 10; and FIG. 1C shows a perspective view of wound filler 10. The array of interconnected ovules may exhibit corner ovules 12, edge ovules 14, and optionally but preferably at least one central ovule 16. Though the views of FIGS. 1A-1C show an array containing 50 rows and 50 columns, it should be understood that the array may be of any reasonable size and may comprise any number of rows and any number of columns sufficient to assist in treating a tissue site. FIG. 1A contains circle D; FIG. 1B contains circle E; and FIG. 1C contains circle F. These circles encompass inset areas that are magnified in FIGS. 1D, 1E, and 1F, respectively. Corner ovules 12, edge ovules 14, and central ovules 16 are also shown in these figures.

Figure 1D:
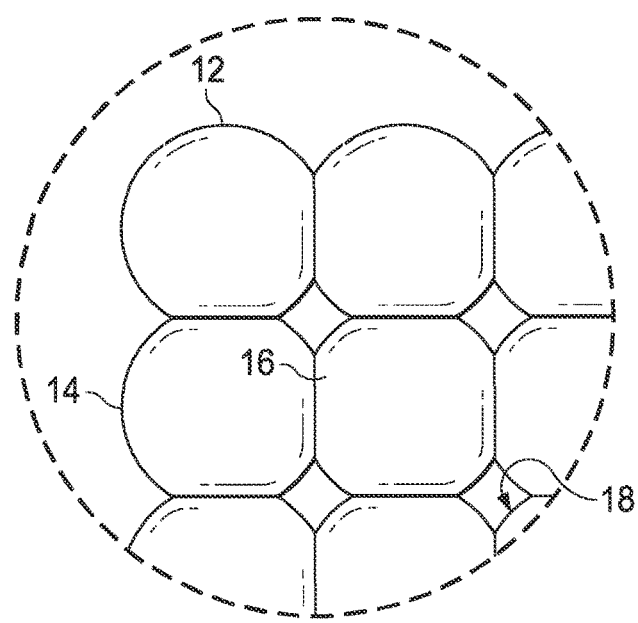
FIGS. 1D-1F are expanded views of insets D, E, and F, from FIGS. 1A, 1B, and 1C, respectively.
Figure 1E:
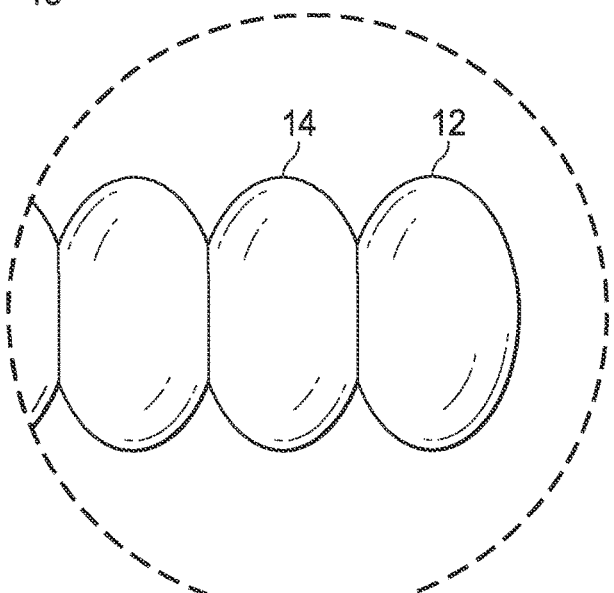

FIGS. 1D and 1E show dimensions of one embodiment of the array of ovules having a truncated ellipsoidal shape, which in this embodiment constitutes a truncated spheroidal shape. Ellipsoids generally have three orthogonal principal axes; spheroids generally are ellipsoids but with two of the three principal axes being approximately equal in length. In these figures, and consistent with the embodiment shown in FIGS. 1A-1C, a principal axis of the ovules or ellipsoids can be oriented substantially perpendicular to the plane of the array. Also as shown in the figures, the other two principal axes can be oriented substantially within the plane of the array. In some embodiments, such as shown in the figures, that substantially perpendicular axis may be the longest principal axis. In some embodiments, such as shown in the figures, the two principal axes other than the longest principal axis may be oriented at approximately a 45° angle to a row direction of the array and at approximately a 45° angle to a column direction of the array, respectively.

In some embodiments, the array may comprise at least four interconnected ovules having truncated ellipsoidal shape that together define at least one fluid pathway 18 through the array. For example, as shown in FIG. 1D, an array of two rows and two columns of interconnected ovules can define a single fluid pathway 18 extending approximately perpendicularly through the plane of the array. In some embodiments, the array may include four corner ovules 12, at least four edge ovules 14, at least one central ovule 16, and at least four fluid pathways 18 interstitially therebetween, for example, each defined by a set of four interconnected ovules. In some embodiments, such as shown in the figures, the array may include at least three columns and at least three rows. In these embodiments, the at least three columns may include two edge columns and at least one central column, and the at least three rows may include two edge rows and at least one central row.

In some embodiments, the wound filler 10 may include a layer having a plurality of fluid pathways therethrough from a first or top surface to a second or bottom surface. In some embodiments, the wound filler 10 may also include an array of interconnected protrusions extending through the layer connecting the top and bottom surfaces, for example with each set of four interconnected protrusions from each of the top and bottom surfaces defining one fluid pathway extending perpendicularly through the array. In some embodiments, each fluid pathway may have four continuously-curved concave sides. Additionally or alternatively, in some embodiments, each fluid pathway may have a parallelogram-shaped cross-section with continuously-curved concave edges.

FIGS. 1D and 1E also show top view and side view, respectively of the truncations of the ellipsoidal (spheroidal) ovules. Each truncation is shown as an approximately flat surface where two ovules interconnect. In some embodiments, each central ovule may be interconnected at four contact surfaces or bond zones, each edge ovule may be interconnected at three contact surfaces or bond zones, and each corner ovule may be interconnected at two contact surfaces or bond zones. In some embodiments, such as embodiments in which the ovules in the array are spheroids each having its longest principal axis substantially perpendicular to the plane of the array, each contact surface or bond zone may be approximately elliptical in shape.

In some embodiments, the interconnected ovules may be polymeric, such as comprised of a polyolefin, a polyester, a polyamide, a polystyrene, a polydiolefin, a polyacrylonitrile, a polysiloxane, or a copolymer or combination thereof. In certain embodiments, the interconnected ovules may be non-adherent to a tissue site. In some embodiments, each of the interconnected ovules has a surface hardness from about 0 Shore A to about 25 Shore A. In some embodiments, the upper surface, the lower surface, or both, of the array of interconnected ovules may exhibit a hardness from about 0 Shore A to about 25 Shore A. In some embodiments not shown in the figures, the upper surface, the lower surface, or both, of the array of interconnected ovules may include a coating disposed thereon that exhibits a hardness of at least 55 Shore A. In embodiments when a coating is present, the coating may be comprised of a cellulosic material, a polyester, a polyamide, a polycarbonate, a perhalogenated polyolefin, an aramid, a polybenzimidazole, a polysulfone, or a copolymer, combination, or cross-linked gel thereof.

In some embodiments not shown in the figures, at least a portion of the interconnected ovules may include one or more grooves on an outer surface of each ovule that extend at least partially in a direction of its longest principal axis. In embodiments where one or more grooves are present, each groove may have an average depth no more than 30% of a diameter of each interconnected ovule along a principal axis direction other than the longest principal axis. Additionally or alternatively, at least a portion of the interconnected ovules may have an external texture, whether in relief or counter-relief, which may be systematic or random, such as texture patterns commercially available from Standex Int'l. Ltd. of London, England.

It can be desirable, in some embodiments, for portions of the ellipsoidal surfaces of the interconnected ovules forming the upper surface of the array, the lower surface of the array, or both, to protrude above/below portions defining the fluid pathways through the array. Without being bound by theory, it is believed that one or more of the sizes of, the shapes of, and the component materials making up the interconnected ovules and defining the fluid pathways therebetween may be tailored to allow negative pressure to be communicated across the array, such as through the fluid pathways without complete collapse under applied negative pressure.

Figure 1F:
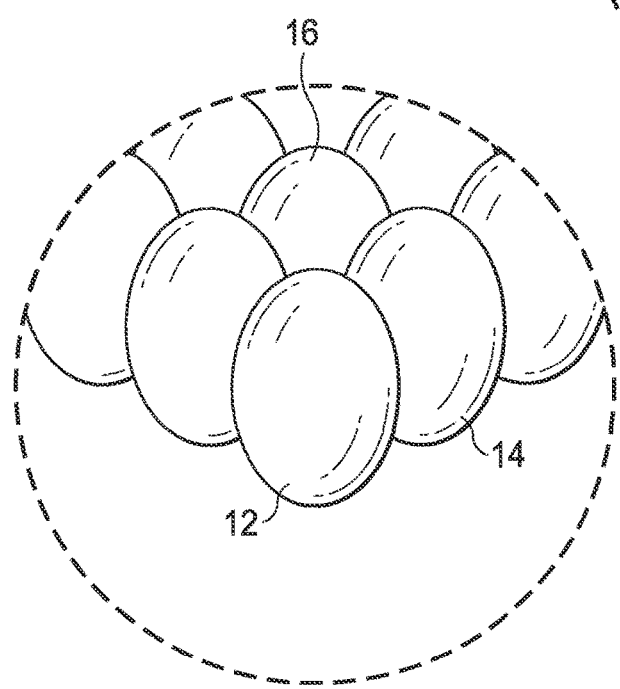

In some embodiments, such as shown in FIGS. 1D-1F, the longest principal axis of each interconnected ovule may be from about 3 mm to about 6 mm. Additionally or alternatively, each principal axis other than the longest principal axis of each interconnected ovule may be from about 2 mm to about 4 mm. In some embodiments, each fluid pathway 18 has a minimum width dimension from about 500 microns to about 1500 microns. In some embodiments, the wound filler 10 may be at least partially, or completely, translucent.

In the embodiment shown in FIGS. 1A-1F, the wound filler 10 includes only a single layer array of interconnected ovules. However, it should be understood that the wound filler 10 can alternatively include two or more layers of arrays of interconnected ovules, and two or more of those layer arrays may interconnect with each other across layers, for example via additional truncations in the ovules. Nevertheless, any interconnection between layers of ovules should maintain the fluid pathways 18 existing through each array or layer, so that a plurality of fluid pathways are retained through the entire wound filler 10.

In some embodiments containing only a single layer array, such as shown in FIGS. 1A-1F, the interconnected ellipsoidal (spheroidal) ovules are truncated only at each surface where the ellipsoids (spheroids) are interconnected. In some embodiments not shown in FIGS. 1A-1F, each interconnected ovule is truncated only at each surface where the ovules are interconnected and at one end of the longest principal axis of the ovule. For example, when tissue site therapy includes use of a wound filler 10 having a top and a bottom surface, and when only one of those surfaces is oriented to contact a tissue site, then the other of those surfaces may constitute the surface at which the end of the longest principal axis is truncated. In some embodiments, the truncation at the one end of the longest principal axis of each ovule can occur at approximately 50% of the length of the longest principal axis. In other embodiments, the truncation at the one end of the longest principal axis of each ovule can occur at between 60% and 90% of the distance from the other end of the longest principal axis. In most embodiments in which each ovule is truncated at one end of the longest principal axis, the truncation may occur approximately perpendicular to the longest principal axis, and thus approximately parallel to the plane of the array.

The wound filler may be made using any viable technique, such as compression or injection molding using one or more pre-made forms. If more than one pre-made form is used, the forms can be combined thereafter, such as by melt-joining or an equivalent technique, to form a single as-synthesized wound filler. However, continuous or semi-continuous manufacture may be employed as an alternative to molding, for example by using a rotary die that can vary its orifice appropriately to allow for extrusion of the complex surfaces of the wound filler materials.

In some embodiments, the wound filler 10 may optionally comprise one or more additional materials. Such optional components may include, for example, active materials such as preservatives, stabilizing agents, plasticizers, matrix strengthening materials, dyestuffs, and combinations thereof. Such optional components may additionally or alternatively include passive materials, for example in situations when ex vivo detection may be important, such as a sufficient amount of magnetic, metal, or ceramic material to allow ready ex vivo detection, such as via an x-ray or MRI apparatus. Additionally or alternatively, the wound filler 10 may comprise one or more additional active materials, for example, antimicrobial agents that may be effective to aid in tissue healing. Non-limiting examples of such active materials may include non-steroidal anti-inflammatory drugs such as acetaminophen, steroids, antimicrobial agents such as penicillins or streptomycins, antiseptics such as chlorhexidine, growth factors such as fibroblast growth factor or platelet derived growth factor, peptides, microRNA, antioxidants, and other well-known therapeutic agents, alone or in combination. If present, such active materials may typically be included at any effective level that show therapeutic efficacy, while preferably not being at such a high level as to significantly counteract any critical or desired physical, chemical, or biological property of the wound filler. Depending upon the therapeutic goal(s), the active material(s) may be loaded at a level of from about 10 wppm to about 10 wt % of the layer(s) in which it(they) is(are) present, for example, from about 50 wppm to about 5 wt % or from about 100 wppm to about 1 wt %.

In some embodiments, the wound filler 10 can have manifolding properties and can be configured to allow fluid removal from a tissue site, fluid instillation to a tissue site, or both, for example by virtue of the plurality of fluid pathways 18 extending through the wound filler 10.

In some embodiments, the wound filler 10 may be configured to be sized by a user to fit a tissue site, for example an overhang wound or compartmented tissue such as a peritoneal or an abdominal cavity. If sizing the wound filler 10 is necessary, excess portions of the wound filler 10 may be removed, for example by cutting or tearing, to attain a wound filler 10 of an appropriate size for the respective tissue site or intended use. In some embodiments, the wound filler 10 may be designed to contain various locations enabling ease of cutting or tearing, such as designated weak points, which may have a smaller cross-array thickness but which would preferably still provide physical connectivity of the array under most if not all operational conditions, when sizing is not necessary.

In some embodiments, a wound filler, such as wound filler 10, can be a separate apparatus used in conjunction with a dressing or other therapy device for providing treatment to a tissue site. In some embodiments, a dressing or other therapy device may include an integral wound filler layer, for example with a use of providing treatment to a tissue site. In preferred embodiments, a wound filler, such as wound filler 10, may function to encourage healing, as indicated by tissue granulation, at a tissue site while simultaneously inhibiting or minimizing ingrowth of tissue into and around the wound filler, thereby allowing removal of the wound filler from the tissue site with little or no pain to a patient.

Figure 2:
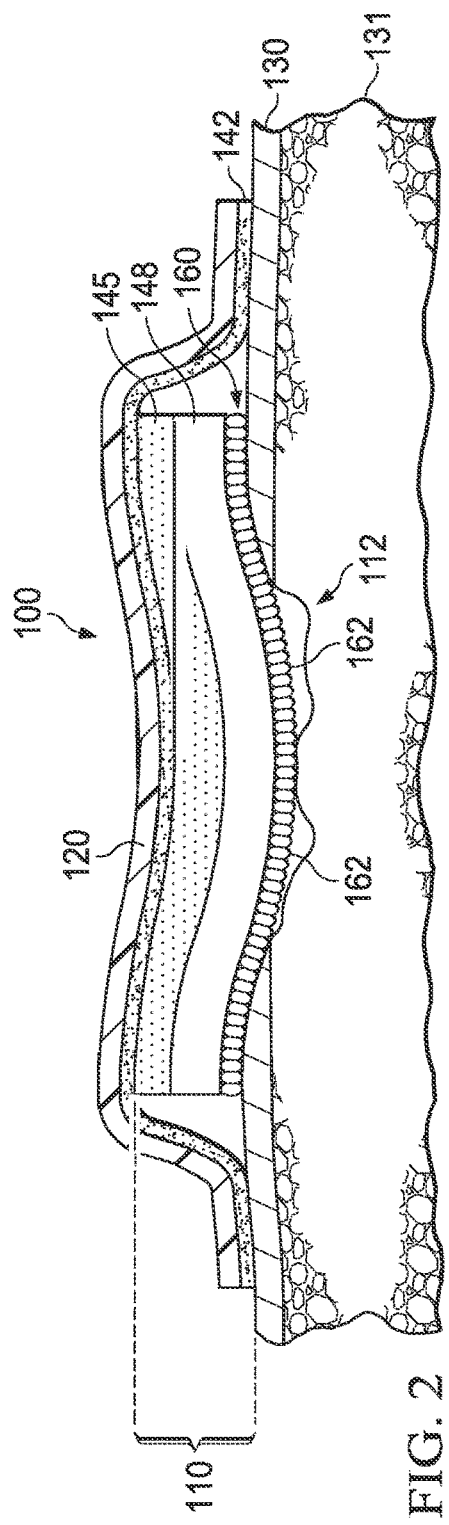
FIG. 2 is a schematic diagram, with a portion in cross-section, of an illustrative device for treating a tissue site.

FIG. 2 shows a dressing 100 including a dressing layer 110. The dressing layer 110 may generally be configured to be positioned on, over, in, adjacent to, or in contact with (collectively, "near") the tissue site.

In various embodiments, the dressing layer 110 may be configured so as to be near a portion of a tissue site, substantially all of a tissue site, or a tissue site in its entirety. If a tissue site is a wound, for example, the dressing layer 110 may partially or completely fill the wound, or may be placed over or near the wound. In various embodiments, the dressing layer 110 may take many forms, and may have many sizes, shapes, or thicknesses depending on a variety of factors, such as the type of treatment being implemented or the nature and size of a tissue site. For example, the size and shape of the dressing layer 110 may be adapted to the contours of deep and irregular shaped tissue sites, may be configured so as to be adaptable to a given shape or contour, or both. Moreover, in some embodiments, any or all of the surfaces of the dressing layer 110 may comprise projections, protrusions, or an uneven, course, or jagged profile that can, for example, induce strains and stresses on a tissue site, which may be effective to promote some granulation at the tissue site.

In some embodiments, the dressing layer 110 may be in substantially sheet form. For example, the dressing layer 110 may comprise a generally planar structure having two opposite-facing planar surfaces and a depth or thickness orthogonal to the planar surfaces. More particularly, for example, the dressing layer 110 may comprise a first or bottom surface opposite a second or top surface. The bottom surface may be adapted to contact a tissue site, having a surface area sufficient to contact an appropriate portion, if not all, of the tissue site. For example, a surface area from about 1 cm² to about 4000 cm² may be suitable for many applications. In various embodiments, the top surface and the bottom surface may have any suitable shape, examples of which include, but are not limited to, triangles, squares, rhombuses, rhomboids, diamonds, rectangles, trapezoids, ellipses, ellipsoids, circles, semi-circles, pie-wedges, ovals, and various polygons having four, five, six, seven, eight, or more sides. These shapes may additionally or alternatively be adaptations of such common shapes. In some embodiments, shapes with typically rounded edges may be altered to be flatter, such as a rounded hexagonal/octagonal shape made by flattening the rounded edges of a circle. Additionally or alternatively, shapes with typically rounded edges may be altered to be sharper, such as a tear-drop shape made by sharpening a rounded end of an ellipse or ellipsoid, or such as an eye shape made by sharpening two rounded, opposing ends of an ellipse or ellipsoid. Further additionally or alternatively, shapes with typically pointed edges may be altered to be more rounded, such as for a blunt-ended triangle. Still further additionally or alternatively, shapes with typically flat edges may be altered to be more rounded, such as by converting the flat sides of any regular polygon to a sinusoidal edge to form a doily shape with an undulating, curvy edge. The shape and area of the bottom surface may be customized to the location and type of tissue site onto which the dressing 100 is to be applied.

There can be various embodiments of the composition of the dressing layer. In some embodiments, the dressing layer 110 may be a single layer; in other embodiments, the dressing layer 110 may represent a multi-layer composite structure. For example, the dressing layer 110 may comprise at least two adjacent layers.

In some examples, two layers of a multi-layer composite may be coupled to each other using any appropriate technique. For example, a lamination process can be used to couple layers together, particularly where neither of the layers to be coupled are fibrous. In some embodiments, an adherent layer containing an adhesive can be used to directly or indirectly couple layers together.

In some multi-layer embodiments, such as shown in FIG. 2, the dressing layer 110 can include an assembly comprising a manifolding layer 148 and a filler layer 160 made from an array of interconnected ovules 162 with a plurality of fluid pathways extending through the array. In some embodiments, filler layer 160 may be similar to wound filler 10 but coupled to manifolding layer 148, and therefore integral to the dressing 100 as part of dressing layer 110. Despite the presence of fluid pathways through the filler layer 160, when coupled, the filler layer 160 may be described as covering the manifolding layer 148, even though fluid is typically meant to be communicated through both the manifolding layer 148 and the filler layer 160. Similarly, any one of the multiple layers of the assembly may include relatively small gaps, for example from fenestrations or perforations, that do not strictly provide coverage of the entire surface area of any other of the multiple layers of the assembly to which they are directly coupled, and yet the one layer is described herein as covering the other layer. Thus, as used herein, the term "cover" and its grammatical variations, should be understood generally to mean substantially cover and should not require every square micron of a macroscopic surface to have intervening material blocking access thereto. In some embodiments, a first or bottom surface of the manifolding layer 148 can be coupled to a second or top surface of the filler layer 160 by an optionally intervening adherent layer (not shown in FIG. 2), which would be considered an additional layer in the assembly of dressing layer 110. When present, the optional adherent layer can individually be configured to allow fluid flow therethrough, thereby fluidly connecting the filler layer 160 and the manifolding layer 148. For example, the optional adherent layer can comprise perforations or fenestrations in order to achieve such a fluid-permissive configuration, while simultaneously maintaining its function of adhering the two layers together.

In various embodiments, the manifolding layer 148, or more generally the assembly comprised within the dressing layer 110, may individually and collectively be configured to allow fluid removal. In such embodiments, the manifolding layer 148 in particular may comprise fluid pathways interconnected so as to improve distribution or collection of fluids. For example, in some embodiments, the manifolding layer 148 may be a porous material having a plurality of interconnected cells or pores. Examples of suitable materials may include open-cell foam, including reticulated foam, or porous tissue collections. In some embodiments, the manifolding layer may comprise or be a polyurethane foam, a polyurethane film, a melt-blow polyurethane, a thermoplastic polyurethane (such as Daltex® Stretch from Don & Low Ltd.), or a combination thereof. Other suitable material may include gauze or felted mat, which generally include pores, edges, or walls adapted to form interconnected fluid pathways. For example, in some embodiments, the manifolding layer 148 may comprise, consist essentially of, or be opencell foam having pore sizes in a range of 400-600 microns. In one non-limiting example, the manifolding layer may be reticulated polyurethane foam.

In various embodiments, the filler layer 160 may include an array of interconnected ovules 162 with a plurality of fluid pathways extending through the array. In these embodiments, the interconnected ovules 162 may be truncated ellipsoids or spheroids, with truncations being at connection surfaces or bond zones between ellipsoids or spheroids. In some embodiments, each ellipsoidal or spheroidal ovule 162 can have a longest primary axis oriented substantially perpendicular to the plane of the filler layer 160 and, in some circumstances, may have an additional truncation at one end of its longest primary axis. In those embodiments in which the additional truncations are present, as shown in FIG. 2, the truncations can form the top surface, proximate to the bottom surface of the manifolding layer 148 to which the array, and thus the filler layer 160, is coupled. One, some, or all of the features, characteristics, and composition of the wound filler 10 shown in FIGS. 1A-1F or described herein can be a feature, characteristic, or composition of the filler layer 160, shown in FIG. 2 in side view, in a similar viewpoint to the wound filler 10 in FIGS. 1B and 1E.

Because of its disposition as the first or bottom surface of the dressing layer 110, the filler layer 160 may comprise or be made from materials suitable for exposure to or implantation within tissue sites. Such materials themselves may cause some levels of granulation or immune response when in contact with tissue sites but are typically not designed to result in extreme edema, widespread immune response, reduction of interstitial fluid flow, or any bodily response that significantly negatively interferes with tissue site treatment. In some embodiments, the filler layer material may be non-adherent. Non-limiting examples of filler layer materials may include a polyolefin, a polyester, a polyamide, a polystyrene, a polydiolefin, a polyacrylonitrile, a polysiloxane, or a copolymer or combination thereof. In some embodiments, the filler layer 160 may comprise a polysiloxane.

In some embodiments, the periodicity of interconnected ovules 162 in the filler layer 160 along the plane of the array may be from about 0.25 mm to about 6 mm, for example from about 0.5 mm to about 1.5 mm, from about 0.25 mm to about 5 mm, from about 0.5 mm to about 5 mm, from about 1 mm to about 5 mm, from about 3 mm to about 6 mm, from about 2 mm to about 4 mm. As used herein, the term "periodicity," with respect to interconnected structures such as ovules, should be understood to mean a repeat unit distance. This repeat unit distance may be measured in any reasonable way. For example, for the interconnected ovules 162 in filler layer 160, the periodicity along the plane of the array can be expressed as a distance between protrusion peak centers, whether along columns or along rows, or as a distance between the through-thickness fluid pathway centers, which may each represent approximately the same periodicity for spheroidal ovules with longest principal axes substantially perpendicular to the plane of the array. An alternative measure of periodicity along the plane of the array may be the length of a principal axis other than the longest principal axis of each interconnected ovule, which would represent a planar array width, whether a column width or a row width, of the truncated ellipsoids or spheroids.

Without being bound by theory, it is believed that a tissue-contacting surface made of non-adherent materials and/or having non-porous protrusions and fluid pathways therethrough, particularly within a certain size range, may reduce, inhibit, or eliminate unintended tissue growth into a dressing. When granulation extends significantly into the dressing layer of a dressing, removal of that dressing to end tissue treatment or at an end of a phase of tissue treatment may cause pain or discomfort to a patient and may include removing some portion of the granulation along with the dressing. By having protrusions and fluid pathways with dimensions falling within particular size ranges, for example, granulation around the protrusions and among the fluid pathways may typically be more easily disengaged during removal of the dressing, and the likelihood of troublesome granulation in-growth can be reduced, inhibited, or eliminated, along with the accompanying pain and discomfort to the patient.

In some embodiments, the assembly containing the manifolding layer 148 and filler layer 160 may be configured to be sized by a user to fit the tissue site; indeed, the dressing layer 110 or the entire dressing 100 itself may be sized to fit the tissue site and disposed at or within a tissue site, for example an overhang wound. In some embodiments, excess portions of the dressing layer 110 or the dressing 100 may be removed, for example by cutting or tearing, to attain a dressing layer 110 or a dressing 100 of an appropriate size.

In some embodiments, at least a portion of the interconnected ovules 162 in the array of the filler layer 160 may comprise grooves along a length of each ovule 162. If present, the portion of the ovules 162 exhibiting grooves may have an average groove width at half-depth from about 0.4 mm to about 1.5 mm, for example from about 0.5 mm to about 1.0 mm. Additionally or alternatively, if present, the grooves may have a depth up to 30% of the ovule width along the plane of the array of the filler layer 160. The grooves, if present, may take any suitable shape in fiber cross-section, examples of which include, but are not limited to, triangles, squares, rhombuses, rhomboids, diamonds, rectangles, trapezoids, ellipses, ellipsoids, circles, semicircles, pie-wedges, ovals, and various polygons having four, five, six, seven, eight, or more sides. These shapes may additionally or alternatively be truncations or adaptations of such common shapes. In some embodiments, shapes with typically rounded edges may be altered to be flatter, such as a rounded hexagonal/octagonal shape made by flattening the rounded edges of a circle. Additionally or alternatively, shapes with typically rounded edges may be altered to be sharper, such as a tear-drop shape made by sharpening a rounded end of an ellipse or ellipsoid, or such as an eye shape made by sharpening two rounded, opposing ends of an ellipse or ellipsoid. Further additionally or alternatively, shapes with typically pointed edges may be altered to be more rounded, such as for a blunt-ended triangle. Still further additionally or alternatively, shapes with typically flat edges may be altered to be more rounded, such as by converting the flat sides of any regular polygon to a sinusoidal edge to form a doily shape with an undulating, curvy edge. Without being bound by theory, it is believed that the presence of ovule grooves may assist in inducing macrostrain and microstrain at the tissue site, for example in tandem with application of negative pressure.

In some embodiments, the manifolding layer 148 may be perforated or fenestrated, particularly in cases where it is desirable to combine application of the dressing 100 containing the manifolding layer 148 with negative-pressure treatment to a tissue site. Additionally or alternatively, the manifolding layer 148 may comprise or be made from an open-cell foam, a mesh, paper, non-woven fibers, woven fibers, or the like. In such embodiments, the perforations, the fenestrations, the porosity, or the interconnectedness of cells in the manifolding layer material may allow the manifolding layer 148 to enable, facilitate, or allow fluid removal from a tissue site, fluid instillation to a tissue site, or both therethrough. In some embodiments, the manifolding layer can comprise or be made from any of a variety of different materials. For example, the manifolding layer 148 may contain a thermoplastic elastomer, a polyurethane, poly (vinyl chloride), a polyester, a polyether, a polystyrene copolymer, or a combination thereof.

In some embodiments, the manifolding layer 148 may comprise an absorbent material adapted to absorb fluid and adapted to reduce, inhibit, or eliminate in vivo granulation, particularly for manifolding layers that are foams or are porous. In one non-limiting example, the absorbent material may comprise a cross-linked hydrogel, such as a hydrophilic poly(vinyl alcohol). The absorbent material may be present within or on one or more surfaces of the manifolding layer.

In some embodiments, such as shown in FIG. 2, the dressing layer 110 may include an absorbent layer 145. For example, the dressing layer 110 may comprise a composite island having one or more absorbent layers. The absorbent layer 145 may comprise a non-woven material of predominantly non-woven fibers, in some embodiments. For example, in various embodiments, the absorbent layer 145 may comprise from about 45 parts to about 100 parts by weight of cellulosic (for example, cellulose ether) fibers and optionally up to about 55 parts by weight of reinforcing fibers. In particular embodiments, the absorbent layer may comprise from about 45 parts to about 95 parts by weight, from about 45 parts to about 90 parts by weight, from about 50 parts to about 90 parts by weight, from about 60 parts to about 90 parts by weight, from about 65 parts to about 85 parts by weight, or from about 70 parts to about 90 parts by weight of cellulosic fibers and about 55 parts to about 10 parts by weight, from about 50 parts to about 10 parts by weight, from about 45 parts to about 10 parts by weight, from about 40 parts to about 10 parts by weight, from about 35 parts to about 15 parts by weight, from about 30 parts to about 10 parts by weight, from about 30 parts to about 15 parts by weight, or from about 25 parts to about 10 parts by weight of reinforcing fibers. In some optional embodiments, biodegradable components may additionally be present in an absorbent layer, for example in amounts from about 1 part to about 20 parts by weight, such as from about 1 part to about 15 parts by weight or from about 1 part to about 10 parts by weight. In some embodiments, absorbent fibers may be comprised of about 80 parts to about 100 parts by weight of cellulosic, for example cellulose ether such as carboxymethyl cellulose, fibers and optionally up to about 20 parts of reinforcing fibers, biodegradable components, or both.

In some embodiments, absorbent material may be absent in or removed from a zone within the absorption layer 145. Such embodiments offer an additional or alternative mechanism enabling at least partial fluid absorptive expansion within the absorption layer 145, which can enable additional degrees of freedom for fluid absorption while creating no or little additional pressure on the tissue site. For example, by creating a central zone in the absorbent layer 145 of the dressing layer 110 that is absent of material, the other portions of the absorbent layer 145 can have extra volume to expand and can optionally experience increased fluid flow within the dressing layer 110, thus rendering the absorbent layer 145 more efficient.

In some embodiments, the absorbent layer 145 may be perforated to increase fluid flow, to reduce time to equilibrium absorption, or both. Such embodiments offer another additional or alternative mechanism enabling additional degrees of freedom for fluid absorption while creating no or little additional pressure on the tissue site.

If cellulosic fibers are present in the absorbent layer 145, the cellulosic fibers may be composed of at least one of carboxymethyl cellulose (CMC), carboxyethyl cellulose, hydroxyethyl cellulose, hydroxypropyl cellulose, hydroxypropylmethyl cellulose, and cellulose ethyl sulphonate (CES) (particularly carboxymethyl cellulose), for example. In some embodiments, the cellulosic component may be at least partially in a salt form, for example, comprising a physiologically acceptable cation such as sodium. CMC is commercially available from a variety of sources, such as under the tradenames WALOCEL™ (sold by The Dow Chemical Company) and CEKOL® (sold by CP Kelco. If reinforcing fibers are present in the absorbent layer 145, for example, the reinforcing fibers may be composed of at least one of non-gelling cellulose, a polyurethane gel, an amide polymer such as Nylon 6,6, an olefin polymer such as HDPE, an ester polymer such as PET, and a modified acrylamide polymer. If biodegradable components are present in the absorbent layer 145, for example, the biodegradable components may be composed of, but not limited to, an alginic acid, an alginate salt, chitosan, chitin, a guar gum, a locust bean gum, a xanthan gum, a karaya gum, gelatin, pectin, a starch derivative such as a dextran, a glycosaminoglycan, a galactomannan, a chondroitin salt, heparin, a heparin salt, collagen, oxidized regenerated cellulose (ORC), hyaluronic acid, a hyaluronate salt, or a combination thereof. For such listed salt components, the salt components may include any reasonable counterions, such as sodium, calcium, ammonium, or the like, or combinations thereof. The biodegradable component(s) can be, for example, in the form of a film or foam, such as open-cell foam, including reticulated foam, or combinations thereof. If in foam form, the average pore size may vary according to needs of a prescribed therapy, for example, from about 400 microns to about 600 microns. Other physico-chemical properties of biodegradable components, such as tensile strength, may be chosen or manipulated, for example, to be suitable to needs of a prescribed treatment.

In some multi-layer embodiments, if an absorbent layer 145 is present, a surface of the absorbent layer 145 not coupled to the manifolding layer 148 can be oriented away from the bottom surface of the dressing layer 110. In some embodiments, it may be advantageous for an absorbent layer to be separated from a tissue site, for example, such that the surface of the absorbent layer not coupled to the manifolding layer can be oriented away from the bottom or tissue-contacting surface of the dressing layer 110.

In some embodiments, particularly if biodegradable components are included, the dressing layer 110 may be characterized as having some biodegradable character or as exhibiting biodegradability. "Biodegradable" and "biodegradability" may individually or collectively refer to a characteristic of a material to disintegrate, degrade, or dissolve upon exposure to physiological fluids or processes, for example, if the dressing layer 110 is applied to a tissue site. For example, in some embodiments, the dressing layer 110 or a material from which the dressing layer 110 is formed may form a gel if contacted with an aqueous medium, such as water, saline, blood, or exudate. Such biodegradability may be exhibited as a result of chemical process or condition, a physical process or condition, or some combination thereof. For example, the biodegradable characteristics of the dressing layer 110 may substantially reduce or eliminate the need to remove the dressing layer 110 from a tissue site to which it is applied. In some embodiments, at least about 90% by weight of the biodegradable component (particularly at least about 95% by weight, at least about 99% by weight, or about 100% by weight) may be disintegrated, degraded, or dissolved within a time period of from about 15 days to about 24 hours (particularly from about 12 days to about 36 hours or from about 10 days to about 48 hours), from introduction into a physiological environment when incubated with simulated physiological fluid at a temperature of about 37° C.

In some embodiments, the dressing 100, and particularly the dressing layer 110, may optionally comprise one or more additional materials. Such optional components may include, for example, active materials such as preservatives, stabilizing agents, plasticizers, matrix strengthening materials, dyestuffs, and combinations thereof.

Additionally or alternatively, the dressing 100, and particularly the dressing layer 110, may comprise one or more additional active materials, for example, antimicrobial agents that may be effective to aid in tissue healing. Non-limiting examples of such active materials may include non-steroidal anti-inflammatory drugs such as acetaminophen, steroids, antimicrobial agents such as penicillins or streptomycins, antiseptics such as chlorhexidine, growth factors such as fibroblast growth factor or platelet derived growth factor, peptides, microRNA, antioxidants, and other well-known therapeutic agents, alone or in combination. If present, such active materials may typically be included at any effective level that show therapeutic efficacy, while preferably not being at such a high level as to significantly counteract any critical or desired physical, chemical, or biological property of the dressing. Depending upon the therapeutic goal, active material may be loaded at a level of from about 10 wppm to about 10 wt % of a layer in which it is present, for example, from about 50 wppm to about 5 wt % or from about 100 wppm to about 1 wt %.

In some embodiments when antimicrobial agents are present, the antimicrobial agents may comprise a safe and effective amount of poly(hexamethylene biguanide) ("PHMB"), which is also known as polyaminopropyl biguanid ("PAPB") and polyhexanide, having the following general formula.

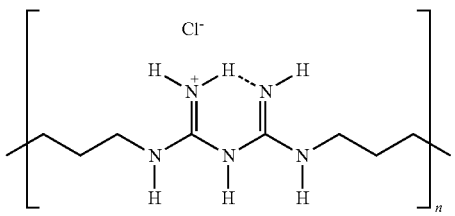

PHMB can be a cationic broad spectrum antimicrobial agent. PHMB may be synthesized by a variety of methods, including polycondensation of sodium dicyanamide and hexamethylenediamine. PHMB is commercially available from a variety of sources. In some embodiments, the PHMB may be present in one or more of the dressing layers at a level of from about 0.005 wt % to about 0.025 wt % of each layer in which it is present, particularly from about 0.007 wt % to about 0.2 wt % or from about 0.008 wt % to about 0.012 wt %, or in some cases at about 0.01 wt %. In some embodiments, the PHMB may be present in the dressing layer 110 at a level of from about 0.05 wt % to about 3 wt % of a layer in which it is present, particularly from about 0.1 wt % to about 2.5 wt %, from about 0.3 wt % to about 2 wt %, from about 0.5 wt % to about 1.5 wt %, or in some cases at about 1 wt %. In alternative embodiments, silver compounds having antimicrobial efficacy may completely or partially replace the PHMB, as desired. In alternative embodiments, silver compounds having antimicrobial efficacy may completely or partially replace the PHMB, as desired.

In some embodiments where CMC is not already present, CMC may be added as a modifier for one or more characteristics of the dressing 100 or dressing layer 110, for example, the rheological, absorbency, and other structural characteristics. CMC may be present in one or more layers of the dressing 100 at any level appropriate to result in the desired absorbency, rheological, or other structural characteristics of the dressing 100.

In some embodiments, the absorbent layer portion 145 of the dressing layer 110, when an absorbent layer is present, may contain a strengthening material, which can improve the handling characteristics of the dressing 100, for example, by decreasing its susceptibility to tearing. The strengthening material may comprise non-gelling cellulose fibers in some examples. Such non-gelling cellulose fibers may be substantially water insoluble and may be produced from cellulose that has not been chemically modified to increase water solubility, for example, as contrasted from carboxymethyl cellulose or other cellulose ethers. Non-gelling cellulose fibers are commercially available, such as under the tradename TENCEL (sold by Lenzing AG). In some embodiments, such fibers may be processed from a commercially-available continuous length, by cutting into lengths from about 0.5 to about 5 cm or from about 2 to about 3 cm in length. The non-gelling cellulose fibers may be present in the absorbent layer 145 at any level appropriate to result in desired physical characteristics of the dressing layer 110 or of the dressing 100. In general, when present, the non-gelling cellulose fibers may comprise from about 1% to about 55% of the layer by weight, particularly from about 5% to about 40% of the layer by weight or from about 10% to about 25% of the layer by weight. In some embodiments, if present, the non-gelling cellulose fibers can be characterized as an additional or alternative reinforcing fiber and can be present in reinforcing fiber amounts.

In some embodiments, the dressing 100 may comprise one or more additional layers. In various embodiments, such additional layers may perform any of a variety of functions including, for example, adherence of the dressing 100 to a tissue site or to surrounding tissues, increasing structural rigidity of the dressing 100, imparting elastic recovery, protection from moisture or other contaminants in the external environment, protection of a tissue surface, delivery of one or more active or other materials to a tissue surface, or combinations thereof. In various embodiments, the additional layers may be conformable to a tissue surface, for example, being capable of conforming such that the appropriate surfaces of the dressing 100 are in substantial contact with a tissue site 112.

For example, in the embodiment of FIG. 2, the dressing 100 comprises a backing layer 120, which may be positioned over the dressing layer 110, to cover the dressing layer 110 at a tissue site 112. The backing layer 120 may have a first or bottom surface and a second or top surface. The backing layer 120 may support the dressing layer 110, for example, such that a top surface of the dressing layer 110 can be proximate to the bottom surface of the backing layer 120. In some embodiments, the top surface of the dressing layer 110 may be in contact with and adhered to the bottom surface of the backing layer 120, for example via adherent layer 142.

In particular embodiments, the backing layer 120 of the dressing 100 may extend beyond the boundaries or edges of the dressing layer 110, so as to exhibit an exposed backing layer margin, which may typically be exhibited on the bottom surface of the backing layer 120. In some embodiments, the backing layer 120 may be non-adherent.

In some embodiments, the backing layer 120 may generally be configured to provide a barrier to microbes, a barrier to external contamination, and protection from physical trauma. For example, the backing layer 120 may be constructed from a material that can reduce evaporative losses and provide a fluid seal between two components or two environments, such as between a therapeutic environment and a local external environment. The backing layer 120 may be formed from a suitable material, such as a polymer, for example, which may comprise or be an elastomeric film or membrane that can provide a seal at a tissue site. In some embodiments, the backing layer 120 may comprise or be a polyurethane. In some embodiments, the backing layer 120 may have a high moisture-vapor transmission rate (MVTR). For example, in such an embodiment, the MVTR may be at least 300 g/m$^2$ per twenty-four hours. For example, the backing layer 120 may comprise a polymer drape, such as a polyurethane film, that may be permeable to water vapor but generally impermeable to liquid water. In some embodiments, the backing layer 120 may have a thickness in the range of about from about 15 to about 50 microns.

In some embodiments, the top surface of the dressing layer 110 may be in contact with and adhered to the bottom surface of the backing layer 120. This adherence may, in some embodiments, result from an adherent layer, such as adherent layer 142 in FIG. 2, disposed between the dressing layer 110 and the backing layer 120, thus constituting direct adherence. Such direct adherence means that the adherent layer 142, or at least the portion disposed between the dressing layer 110 and the backing layer 120, can be comprised of one or more different kinds of physical or chemical adhesive compositions. The adherent layer 142 or portion thereof disposed between the dressing layer 110 and the backing layer 120, in some embodiments, may not directly contact a tissue site. For example, in embodiments with a backing layer margin extending beyond the dressing layer 110, the adherent layer 142 may typically extend out to cover all or part of the backing layer margin. In such embodiments, the portion of the adherent layer on the margin may adhere the dressing 100 to tissue proximate to a tissue site 112, such as epidermis 130 in FIG. 2. Adherents that may directly contact tissue or that may be exposed to a treatment environment can typically have additional requirements, such as biocompatibility, and may be selected from a smaller list of physical or chemical adhesive compositions.

In some embodiments, such as where an adherent layer 142 is an external layer in the dressing 100, for example to adhere the dressing 100 to epidermis 130, to sub-epidermal layer 131, or to a tissue site 112, the adherent layer can be releasably coupled to a release liner configured for removal before application to a tissue site, for example.

Adherence between the dressing layer 110 and the backing layer 120 may additionally or alternatively be indirect. For example, in some embodiments with a backing layer margin extending beyond the dressing layer 110, the adherent layer may be disposed on the backing layer margin and extend further over some portion of the dressing layer 110, such as the margin of the dressing layer 110. If this occurs without an adherent layer between the backing layer 120 and the dressing layer 110, the adherent layer may be said to indirectly adhere those layers, because those layers are each adhered to the adherent layer but not directly to each other. Such a configuration can allow an absorbent portion of the dressing layer 110 to expand differentially from the backing layer 120, for instance enabling relatively high levels of absorption of fluid with additional degrees of freedom.

In particular embodiments, any adherent layers in the dressing 100, for example whether coupled to the optional absorbent layer 145, the manifolding layer 148, the backing layer 120, or any other layer in the dressing 100, may comprise a hydrocolloid material, a hydrogel, a silicone adhesive, a silicone gel, an acrylic adhesive, a vegetable-based adhesive, an animal-based adhesive, or a combination or copolymer thereof.

Additionally, in some embodiments, the dressing 100 may further comprise one or more secondary layers, for example, positioned between the dressing layer 110 and the backing layer 120. In some embodiments, a secondary layer may be an additional manifolding layer, which may comprise fluid pathways interconnected so as to improve distribution or collection of fluids. For example, in some embodiments, a secondary layer may be a porous material having a plurality of interconnected cells or pores. Examples of suitable materials for the secondary manifolding layer may include open-cell foam, such as reticulated foam, or porous tissue collections. Other suitable porous material may include gauze or felted mat, which generally include pores, edges, or walls adapted to form interconnected fluid pathways. For example, in some embodiments, a secondary layer may comprise or consist essentially of foam having pore sizes in a range of 400-600 microns. In one non-limiting example, a secondary layer may comprise or be reticulated polyurethane foam.

In some embodiments having a secondary layer, the secondary layer may comprise or be an absorbent layer or may be characterized as exhibiting absorbency. For example, the secondary layer may exhibit an absorbency of at least 3 g saline/g, particularly at least 5 g saline/g, from 5 to 50 g saline/g, from 8 to 40 g saline/g, or from 8 to 20 g saline/g. In some embodiments, the secondary layer may be hydrophilic. In an example in which the secondary layer may be hydrophilic, the secondary layer may also wick fluid away from a dressing layer 110. In such embodiments, the wicking properties of the secondary layer may draw fluid away from dressing layer 110 by capillary flow or other wicking mechanisms. An example of a hydrophilic foam is a polyvinyl alcohol, open-cell foam. Other hydrophilic foams may include those made from or containing a polyester, a polyether, or a polyurethane. Additional or alternative foams that may exhibit hydrophilic characteristics include hydrophobic foams that have been treated or coated to provide hydrophilicity.

Also disclosed herein are methods of treating a tissue site, for example, in the context of various therapies, such as eliminating, minimizing, or reducing edema and/or increasing interstitial fluid flow. In some embodiments, the tissue site may be a compartmented tissue site, such as an overhang wound or a peritoneal or abdominal cavity. In some embodiments, the tissue site may be a surface tissue site, such as a burn, a graft, or a post-operative wound. In some embodiments, the tissue site may be a tunnel wound site, such as a puncture or a fistula.

In some embodiments, a therapy or treatment method may comprise applying the wound filler 10 or the dressing layer 110 comprising a filler layer 160 to a tissue site. The wound filler 10 or dressing layer 110 may be used to treat any of a variety of tissue sites, such as those occurring from trauma, surgery, or disease. For example, the wound filler 10 or dressing layer 110 may be placed within, over, on, or otherwise proximate to a tissue site. Additionally, in some embodiments, a cover such as the backing layer 120 may be placed over the dressing layer 110 and sealed to an attachment surface near the tissue site. For example, the backing layer 120 may be sealed to undamaged epidermis 130 peripheral to a tissue site 112. In some embodiments, the wound filler 10 may be positioned and a dressing layer 110 may be positioned after the wound filler 10 has been positioned. In some embodiments, the backing layer 120 can provide a sealed therapeutic environment proximate to a tissue site containing the wound filler 10 and/or the dressing layer 110, thereby substantially isolating the tissue site from the external environment.

In some embodiments, the therapy or treatment method may comprise applying a wound filler 10, or a dressing 100 containing a filler layer 160, to a tissue site for a period of time. FIGS. 1A-1F show an illustrative embodiment of a wound filler 10, and FIG. 2 shows an illustrative embodiment of a dressing 100 containing a filler layer 160, that may be used in such a treatment. Though FIG. 2 depicts the dressing 100 being deployed at a tissue site 112, such as a burn or a graft wound, the dressing 100 may additionally or alternatively be used in conjunction with other types of tissue sites, such as a post-operative incision, compartmented tissue, a tunnel wound, or the like. Similarly, though FIG. 2 depicts a therapy or treatment method without application of negative pressure and without provision for an instillation fluid, the dressing 100, or a wound filler 10, may additionally or alternatively be used or be modified for use in conjunction with other therapies or treatments, such as those including application of negative pressure, those including provision of an instillation fluid, or those including both.

Referring again to FIG. 2, dressing 100 is shown as comprising the dressing layer 110, the backing layer 120, and an adherent layer 142 coupling the dressing layer 110 and the backing layer 120. Dressing layer 110 includes an assembly of a manifolding layer 148 and a filler layer 160 containing an array of interconnected ovules 162 and fluid pathways extending substantially perpendicular through the array. In the example of FIG. 2, the dressing layer 110 is shown as also including an optional absorbent layer, such as absorbent layer 145. The filler layer 160 is shown as being in contact with the tissue site 112, which is illustrated as being a surface wound transecting the epidermis 130 and extending into layer 131. Layer 131 may represent the dermis or any dermal tissue below the epidermis 130, or it may represent one or more other internal bodily structures, such as muscles, tendons, ligaments, cartilage, bones, connective tissue, adipose tissue, neural tissue, vascular tissue, connective tissue, internal organs, or the like.

Figure 3:
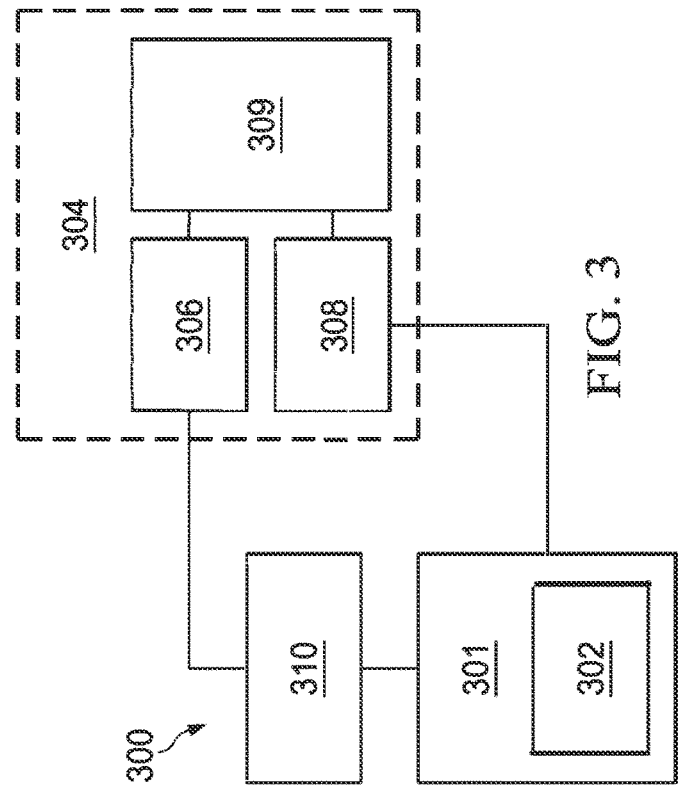
FIG. 3 is a functional block diagram of an example embodiment of a therapy system that can deliver negative pressure as well as a treatment fluid to a tissue site and can manage fluids in accordance with this specification.

FIG. 3 is a simplified functional block diagram of an example embodiment of a therapy system 300 that can provide negative-pressure therapy, optionally along with instillation of topical treatment solutions, to a tissue site in accordance with this specification.

The therapy system 300 may include a therapy unit 304 and a treatment device 301 including a dressing 100. In some embodiments, the therapy unit 304 may include a negative-pressure source, such as negative-pressure source 306, optionally a fluid source, such as fluid source 308, and a regulator or controller 309. In other embodiments, the therapy unit 304 may include the negative-pressure source 306, while the optional fluid source 308 and/or the controller 309 may be freestanding, separate units. The therapy system 300 may optionally also include additional components, such as a container 310, which may be coupled to or in fluid communication with at least the treatment device 301, the dressing 100, the therapy unit 304, and the negative-pressure source 306, whether directly or indirectly. In some embodiments, the treatment device 301 may include a wound filler 10, separate from but in addition to the dressing 100. In some embodiments, a filler layer 160 may be integral with the dressing 100.

Components of the therapy system 300 may be fluidly coupled to each other to provide a path for transferring fluids (i.e., liquid and/or gas) between the components. For example, components may be fluidly coupled through a fluid conductor, such as a tube. A "tube," as used herein, broadly includes a tube, pipe, hose, conduit, or other structure with one or more lumina adapted to convey a fluid between two ends. Typically, a tube is an elongated, cylindrical structure with some flexibility, but the geometry and rigidity may vary. In some embodiments, components may also be coupled by virtue of physical proximity, being integral to a single structure, or being formed from the same piece of material. Moreover, some fluid conductors may be molded into or otherwise integrally combined with other components. Coupling may also include mechanical, thermal, electrical, or chemical coupling (such as a chemical bond) in some contexts. For example, a tube may mechanically and fluidly couple the treatment device 301 to the therapy unit 304 in some embodiments. In general, components of the therapy system 300 may be coupled directly or indirectly.

The negative-pressure source 306 may be configured to be coupled to a distribution component, such as the dressing 100, for example. In general, a distribution component may refer to any complementary or ancillary component configured to be fluidly coupled to a negative-pressure supply in a fluid path between a negative-pressure supply and a tissue site. A distribution component is preferably detachable, and may be disposable, reusable, or recyclable. For example, the dressing 100 of the treatment device 301 may be fluidly coupled to the negative-pressure source 306 of the therapy unit 304, as illustrated in FIG. 3. In some embodiments, the treatment device 301 may include the dressing 100, as well as additional tissue interfaces, fluid conduits, and/or a cover. In some embodiments, a dressing interface may facilitate coupling the negative-pressure source 306 to the dressing 100 of the treatment device 301. For example, such a dressing interface may be a SENSAT.R.A.C.™ Pad, VERA-T.R.A.C.™ Pad, or VERAT.R.A.C.™ Duo Tubing Set available from KCI of San Antonio, Texas.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

"Negative pressure" generally refers to a pressure less than a local ambient pressure, such as the ambient pressure in a local environment external to a sealed therapeutic environment provided by the treatment device 301 or the dressing 100. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.67 kPa) and −300 mm Hg (−39.9 kPa).

A negative-pressure supply, such as the negative-pressure source 306 of the therapy unit 304, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure supply may be housed within or used in conjunction with other components, such as sensors, processing units, alarm indicators, memory, databases, software, display devices, or user interfaces that further facilitate therapy, such as through the use of therapy unit 304. A negative-pressure supply may also have one or more supply ports configured to facilitate coupling and de-coupling the negative-pressure supply to one or more distribution components.

In some embodiments, the therapy system 300 may include one or more sensors, such as a pressure sensor, an electric sensor, a temperature sensor, a pH sensor, a relative humidity sensor, or a combination thereof, to measure one or more operating parameters and provide feedback signals to the controller 309 indicative of the operating parameters. In some embodiments if present, the pressure sensor may also be coupled, or configured to be coupled, to a distribution component and to the negative-pressure source 306, which may, for example, include wireless connection. Additionally or alternatively, a sensor may be configured to provide information to a person, who can then manually control one or more operating parameters externally. Sensors, such as pressure sensors or electric sensors, are generally known in the art as any apparatus operable to detect or measure a physical phenomenon or property, and generally provide a signal indicative of the phenomenon or property that is detected or measured. If present, a pressure sensor may be a transducer configured to measure pressure in a pneumatic pathway and convert the measurement to a signal indicative of the pressure measured, in some embodiments. If present, for example, a pressure sensor may be a piezoresistive strain gauge in some embodiments. If present, an electric sensor may optionally measure operating parameters of the negative-pressure source 306, such as voltage or current, in some embodiments. Also if present, the signals from a pressure sensor and an electric sensor may be suitable as an input signal to the controller 309, but some signal conditioning may be appropriate in some embodiments. For example, in such embodiments the signal may need to be filtered or amplified before it can be processed by the controller 309. Typically in such embodiments, the signal is an electrical signal, but may be represented in other forms, such as an optical signal. If a sensor is meant to monitor conditions at or near a tissue site or sealed volume, then it may be advantageous for the sensor to be placed as close as practical or possible to the site(s) desired to be monitored. In various embodiments, if present, a pressure sensor may be placed in a conduit in fluid communication with the negative-pressure source 306 but proximate to the sealed volume, for example on or in the wound filler 10, if present, or near, on, or in one or more layers of the dressing 100.

The therapy system 300 may optionally also include a source of instillation fluid or solution. For example, a fluid source 308 may be fluidly coupled to the treatment device 301, and thus the dressing 100, as illustrated in the example embodiment of FIG. 3. The fluid source 308 may be fluidly coupled to a positive-pressure source, the negative-pressure source 306, or both in some embodiments. A regulator, such as an instillation regulator, may also be fluidly coupled to the fluid source 308 and the treatment device 301 to ensure proper dosage of instillation solution to a tissue site. For example, the instillation regulator may comprise a piston that can be pneumatically actuated by the negative-pressure source 306 to draw instillation solution from the fluid source 308 during a negative-pressure interval and to instill the solution to the dressing 100 during a venting interval. Additionally or alternatively, the controller 309 may be coupled to the negative-pressure source 306, the positive-pressure source, or both, to control dosage of instillation solution to a tissue site. In some embodiments, an instillation regulator may be fluidly coupled to the negative-pressure source 306 through the treatment device 301, and thus through the dressing 100.

The fluid source 308 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, saline solutions, and isotonic solutions.

A controller, such as the controller 309, may be a microprocessor or computer programmed to operate one or more components of the therapy system 300, such as the negative-pressure source 306 and the fluid source 308. In some embodiments, for example, the controller 309 may be a microcontroller, which generally comprises an integrated circuit containing a processor core and a memory programmed to directly or indirectly control one or more operating parameters of the therapy system 300. Operating parameters may include the power applied to the negative-pressure source 306, the pressure generated by the negative-pressure source 306, or the pressure distributed to the treatment device 301, for example. Additional operating parameters may include the power applied to the fluid source 308, flow rate of instillation fluid provided by the fluid source 308, or volume of fluid distributed to the treatment device 301. The controller 309 is also preferably configured to receive one or more input signals, such as a feedback signal, and programmed to modify one or more operating parameters based on the input signals.

In some embodiments, the negative-pressure source 306, fluid source 308, controller 309, and container 310 may be integrated within a single therapy unit, such as therapy unit 304. For example, the therapy system 300 may therefore include the treatment device 301 along with a therapy unit 304 such as a V.A.C.ULTA™ therapy unit, V.A.C.IN-STILL™ wound therapy system, INFOV.A.C.™ therapy unit, each available from KCI of San Antonio, Texas, or other suitable therapy units or systems. For example, in some embodiments, the therapy unit 304 may comprise or consist essentially of a V.A.C.ULTA™ unit, which may include software modules specific to negative-pressure therapy in combination with fluid instillation therapy, and for use with specific types of tissue sites. Alternatively, any other device capable of providing negative-pressure therapy may be suitable along with any mechanical fluid instillation device, or any negative-pressure therapy device in combination with a manually-managed fluid instillation source, such as a gravity-fed fluid vessel, manual fluid pump, or monitored IV bag or bottle.

Figure 4:
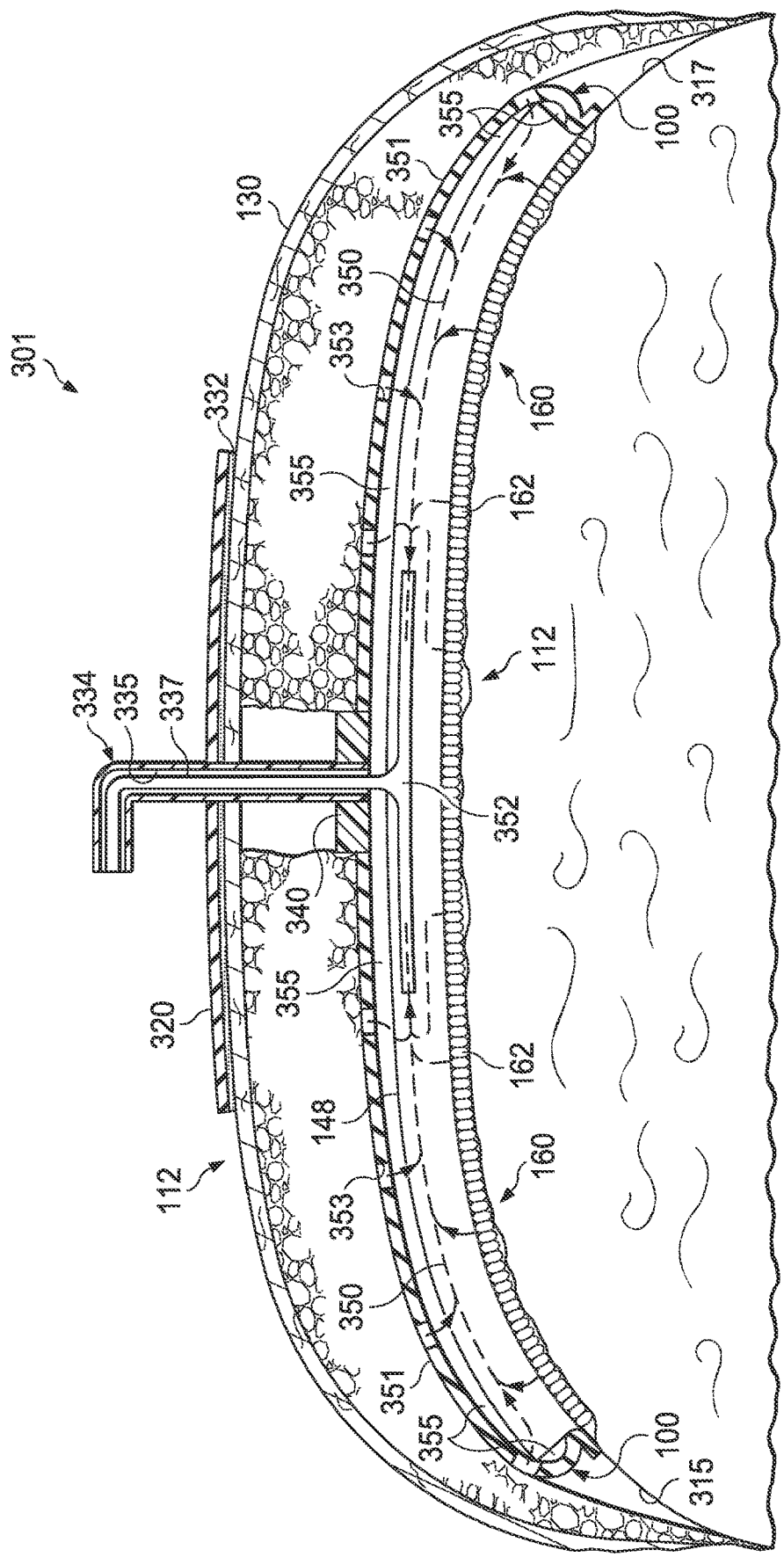
FIG. 4 is a schematic diagram, with a portion in cross-section, of an illustrative device containing a dressing with an integral wound filler sheet for treating an abdominal cavity that may be associated with some embodiments of the therapy system of FIG. 3.

FIG. 4 is a schematic diagram illustrating additional details that may be associated with some embodiments of the treatment device 301. The treatment device 301 of FIG. 4 is applied to another example of the tissue site 112. In this illustrative embodiment, the tissue site 112 may include tissue in a body cavity, such as an abdominal cavity. The tissue site 112 may include abdominal contents or tissue proximate the abdominal cavity. Treatment of the tissue site 112 may include removal of fluids, e.g., ascites, protection of the abdominal cavity, or negative-pressure therapy.

As shown in FIG. 4, the dressing 100 may be disposed near, or within, a tissue site 112, which may be a compartmented site such as a peritoneal or an abdominal cavity, in order to treat the tissue site 112. In some abdominal cavities, for example, the dressing 100 may be supported by the abdominal contents, which can be generalized to most compartmented tissue sites. As depicted, a first portion of the dressing 100 may be positioned in or proximate to a first paracolic gutter 315, and a second portion of the dressing 100 may be placed in or proximate to a second paracolic gutter 317. The first paracolic gutter 315 and the second paracolic gutter 317 may each be, for example, an open space on opposing sides of the abdominal cavity among the abdominal contents. The first paracolic gutter 315 may be laterally disposed from the second paracolic gutter 317 or otherwise located on an opposite side of the tissue site 112 from the second paracolic gutter 317. Although FIG. 4 depicts the treatment device 301 deployed at an abdominal cavity, the treatment device 301 and therapy system 300 may be used at other types of tissue sites, for example in which tissue contacts the treatment device 301, or particularly the dressing 100, on both a first surface and a second surface facing away from the first surface. Non-limiting examples of such tissue sites can include compartmented wounds, overhang wounds, tunnel wounds, flaps, or the like.

In some embodiments, the treatment device 301 may further include a cover 320 for providing a fluid seal over the tissue site 112. In some embodiments, the cover 320 may generally be configured to provide a barrier to microbes, a barrier to external contamination, and protection from physical trauma. For example, the cover 320 may be constructed from a material that can reduce evaporative losses and provide a fluid seal between two components or two environments, such as between a therapeutic environment and a local external environment. The cover 320 may be formed from a suitable material, such as a polymer, for example, which may comprise or be an elastomeric film or membrane that can provide a seal at a tissue site. In examples involving application of negative pressure to a tissue site, the cover can provide a seal adequate to maintain negative pressure at a tissue site for a given negative-pressure source 306. In some embodiments, the cover 320 may comprise or consist essentially of polyurethane. In some embodiments, the cover 320 may have a high moisture-vapor transmission rate (MVTR). For example, in such an embodiment, the MVTR may be at least 300 g/m² per twenty-four hours. For example, the cover 320 may comprise a polymer drape, such as a polyurethane film, that may be permeable to water vapor but generally impermeable to liquid water. In some embodiments, the cover 320 may have a thickness in the range of about from about 15 to about 50 microns. For permeable materials, the permeability generally should be low enough that a desired negative pressure may be maintained.

An attachment device, such as attachment device 332, may be used to attach the cover 320 to an attachment surface of a tissue site 112, such as the epidermis 130 of a patient. The attachment device 332 may be used to attach the cover 320 to a gasket, or another sealing member or cover. The attachment device 332 may take any of a variety of suitable forms. For example, an attachment device may be a medically-acceptable, pressure-sensitive adhesive that extends about a periphery, a portion, or an entire sealing member or cover. In some embodiments, for example, some or all of the cover 320 may be coated with an adherent layer, such as comprising an acrylic adhesive, having a coating weight between 25 and 65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The illustrative systems and devices herein may optionally allow for the irrigation and washing out of a tissue site 112, for example a compartmented site such as a peritoneal or an abdominal cavity, with the controlled and regulated introduction of fluid. In some instances, it may be necessary to wash or cleanse a contaminated abdominal cavity, for example as a result of a perforated colon or sepsis. The therapy system 300 can provide means to instill fluid into an open abdomen to cleanse the abdominal contents, including reaching areas such as the small bowel loops, pancreas, etc. Additionally, the treatment device 301 and the therapy system 300 may provide temporary closure to an open abdomen, while optionally allowing for removal of fluid, reduction of edema, and/or increase in interstitial fluid flow. Thus, the therapy system 300 may provide the capability of performing washouts of a tissue site, such as a peritoneal or abdominal cavity, without having to repeatedly remove one or more dressings applied to the tissue site of a patient or bringing the patient into the operating room for manual fluid introduction procedures. The therapy system 300 may thus be able to provide a controlled and regulated full abdominal wash, for example via instillation of a therapeutic fluid, as well as have the capability to provide a targeted wash to certain areas within the abdomen when required. Some embodiments of the therapy system 300, and more particularly the dressing 100, may also provide support and maintenance of the fascial domain of an abdominal cavity, for example, and provide overall protection to the abdominal contents.

In some embodiments, the therapy system 300 may also include an interface for fluidly connecting the dressing 100 and other portions of the treatment device 301 to a conduit 334, as shown in FIG. 4. The interface may include a connector, which may comprise or be a part of a negative-pressure connector subsystem. Alternatively, the interface may be partially or fully embedded within a portion of the dressing 100, or configured in any other way possible for fluidly connecting the treatment device 301 to a therapy unit, such as the therapy unit 304 of FIG. 3. The conduit 334 may be fluidly coupled to negative-pressure source 306 and/or fluid source 308 of the therapy unit 304 for providing negative pressure and/or treatment fluid, respectively, to the treatment device 301. In some embodiments, the conduit 334 may include two substantially parallel, fluidly-isolated conduits, one of which for fluidly coupling the treatment device 301 to the negative-pressure source 306 and the other for fluidly coupling the treatment device 301 to the fluid source 308. Thus, in some embodiments, the conduit 334 may be a multi-lumen conduit with both a negative-pressure lumen 335 and a fluid withdrawal lumen 337. In some other illustrative embodiments, the conduit 334 may be replaced with two separate conduits, one containing a negative-pressure lumen and the other containing a fluid withdrawal lumen. In embodiments enabling fluid instillation, fluid withdrawal lumen 337 can be temporarily or intermittently repurposed to provide instillation fluid, instead of withdrawing fluid, in which situations fluid withdrawal lumen 337 can alternatively be referred to as a fluid supply lumen. In other embodiments enabling fluid instillation, the conduit 334 may be a multi-lumen conduit with a negative-pressure lumen 335, a fluid withdrawal lumen 337 in fluid communication with container 310, and a separate fluid supply lumen (not pictured in FIG. 4) in fluid communication with fluid source 308, which may be separate from container 310. In such multi-lumen embodiments, the negative-pressure, fluid withdrawal, and fluid supply lumens may be together within the same conduit 334 or may be in three separate conduits or in two separate conduits, for example with the fluid supply lumen in one conduit and the negative-pressure lumen 335 and the fluid withdrawal lumen 337 together in the other conduit.

In some embodiments, the therapy system 300 may further include a filler material 340, such as a portion of foam, disposed between the liquid-impermeable layer 351 and the cover 320. The filler material 340 may be part of the interface and may be sized to fill the portion of abdominal volume beneath or surrounding an incision or opening into abdomen from the skin layers, such as a portion of abdominal cavity. In some embodiments, the filler material 340 may contain within it, or may itself serve as, a distribution manifold for negative pressure. For example, in some embodiments, the filler material 340 may be positioned between the liquid-impermeable layer 351 and the cover 320, and a negative pressure lumen or conduit, such as negative-pressure lumen 335, may be pneumatically connected to the cover 320. As a result, fluid removal may occur from the layers of the treatment device 301 through the filler material 340 positioned atop liquid-impermeable layer 351, and into the negative-pressure lumen 335. In some embodiments, the filler material may include a three-dimensional woven or non-woven fabric, such as TDL2 or TL4, commercially available from Libeltex of Meulebeke, Belgium, or 3DXD or 4DXD spacer fabrics, commercially available from Baltex of Derbyshire, England, or reticulated polyurethane foam such as found in GRANUFOAM™ Dressing or V.A.C. VERAFLO™ Dressing, both available from KCI of San Antonio, Texas.

In FIG. 4, the dressing 100 is shown as comprising an assembly of a manifolding layer 148 and a filler layer 160 made from an array of interconnected ovules 162 with a plurality of fluid pathways extending through the array, between the ovules. Although not depicted in FIG. 4, an absorbent layer, similar to the absorbent layer 145 shown in FIG. 2, may be included in some embodiments as an optional secondary layer of the dressing 100. If present, in some embodiments, an absorbent layer may be positioned between manifolding layer 148 and filler layer 160. Additionally or alternatively in some embodiments, if present, an absorbent layer may be positioned on the manifolding layer 148 on a surface opposite the filler layer 160 and may or may not be coupled to the manifolding layer 148.

By virtue of the fluid removal application of the treatment device 301, facilitated by fluid connection to the negative-pressure source 306, the manifolding layer 148, but more generally the assembly further including filler layer 160, may individually and collectively be configured to allow fluid removal and optionally also to allow fluid instillation. Thus, the manifolding layer 148 in particular may comprise fluid pathways, such as fluid removal pathways 350, interconnected so as to improve distribution or collection of fluids. Manifolding layer 148 may be made of a porous material having a plurality of interconnected cells or pores. Such manifolding materials may promote development of granulation tissue at a tissue site, particularly when pressure is reduced within a sealed therapeutic environment. In some embodiments, however, increased development granulation tissue at a tissue site may not be an objective, or granulation ingrowth into portions of the dressing may be reduced, inhibited, or prevented. For example, the dimensions, shape, or chemical composition of the protrusions from the ovules 162 in the filler layer 160, and/or the dimensions or shape of the fluid pathways between the ovules 162 in the filler layer 160, may assist in reducing, inhibiting, or preventing granulation ingrowth into portions of the dressing 100 or the treatment device 301.

The dressing 100 may include one or more liquid-impermeable layers, such as liquid-impermeable layer 351. The liquid-impermeable layer 351 may be formed with fenestrations 353. "Liquid-impermeable" with respect to "liquid-impermeable layers" means that the layers are formed with a liquid-impermeable material. Thus, although formed with a liquid-impermeable material, the layer may be liquid-permeable when fenestrated, but nonetheless is referred to as a liquid-impermeable layer. The fenestrations 353 may take many shapes or combinations of shapes, including circular apertures, elliptical apertures, rectangular openings, or polygons, for example. The fenestrations 353 are presented in this illustrative embodiment as slits, or linear cuts. In some embodiments, the liquid-impermeable layer 351 may be sealingly coupled to the assembly of the manifolding layer 148 and the filler layer 160 in any suitable manner, for example, without limitation, through chemical means or physical means or both, such as by welding, bonding, adhesives, cements, or other bonding mechanisms. This sealing coupling of the liquid-impermeable layer 351 may include wrapping around portions of the assembly, for example covering all exposed surfaces of the manifolding layer 148 or covering all surfaces of the assembly except for the filler layer 160, as shown in FIG. 4. The liquid-impermeable layer 351 may be adapted to be positioned between otherwise exposed surfaces of the manifolding layer 148 and the tissue site 112. Additionally or alternatively, if the assembly of layers includes an absorbent layer disposed on a surface of the manifolding layer 148 not facing toward the filler layer 160, then the liquid-impermeable layer 351 may be adapted to be positioned between otherwise exposed surfaces of the absorbent layer and the tissue site 112. In some embodiments, liquid-impermeable layers may function to distance other layers, such as manifolding layers, from direct contact with a tissue site, for example to reduce, inhibit, or prevent granulation ingrowth into those layers. The liquid-impermeable layer 351 may comprise a non-adherent material, such as a medical drape, capable of inhibiting tissue from adhering to the non-adherent material. For example, in some embodiments, the liquid-impermeable layer 351 may comprise a breathable polyurethane film.

Although not necessarily depicted in FIG. 4, a therapy method including fluid instillation can occur by periodically stopping application of negative pressure through the fluid withdrawal lumen 337 and initiating liquid supply through the same lumen, which can then alternatively be termed a fluid supply lumen. The negative-pressure lumen 335 may or may not experience an immediate halt in negative pressure application in such fluid instillation embodiments. In such embodiments, the manifolding layer 148 can function both as fluid removal assembly and the optional fluid installation matrix, thereby enabling instillation fluid to be provided to the chamber 355, through the fenestrations 353 in the liquid-impermeable layer 351 and ultimately to the tissue site 112.

As shown in FIG. 4, the sealing coupling between the liquid-impermeable layer 351 and the assembly of the manifolding layer 148 and the filler layer 160 may form a chamber 355. In some embodiments, the chamber 355 may enable the manifolding layer 148 to more efficiently communicate negative pressure and to allow removal of fluids such as exudates from the tissue site 112, and optionally also to function as an instillation matrix to deliver instillation fluid to the tissue site 112. These manifolding functions of the manifolding layer 148 may be seen in the tortuosity of the fluid removal pathways 350 that flow through the fenestrations 353 of the liquid-impermeable layer 351, into the chamber 355, optionally also through the fluid pathways defined by interconnected ovules 162 in filler layer 160, into the manifolding layer 148, and into fluid removal tubes positioned in a central region of the manifolding layer 148 and which are fluidly connected to the fluid withdrawal lumen 337.

In some embodiments, the plurality of fluid removal pathways 350 may be fluidly coupled to a fluid removal hub 352, which is optional but depicted in FIG. 4. The optional fluid removal hub 352 may serve as a distribution mechanism for communicating negative pressure to each of the fluid removal pathways 350 from the interface and the negative-pressure source 306. The fluid removal pathways 350 may take the form of numerous different shapes or be formed from a variety of materials. Multi-lumen tubes may additionally or alternatively make up a portion of the fluid removal pathways 350. Each of the different forms and configurations of fluid removal pathways 350 may also apply to fluid delivery tubes or to an instillation matrix, as applicable, especially in embodiments in which instillation fluid and negative pressure are not alternated using similar pathways but in reverse directions.

Figure 5:
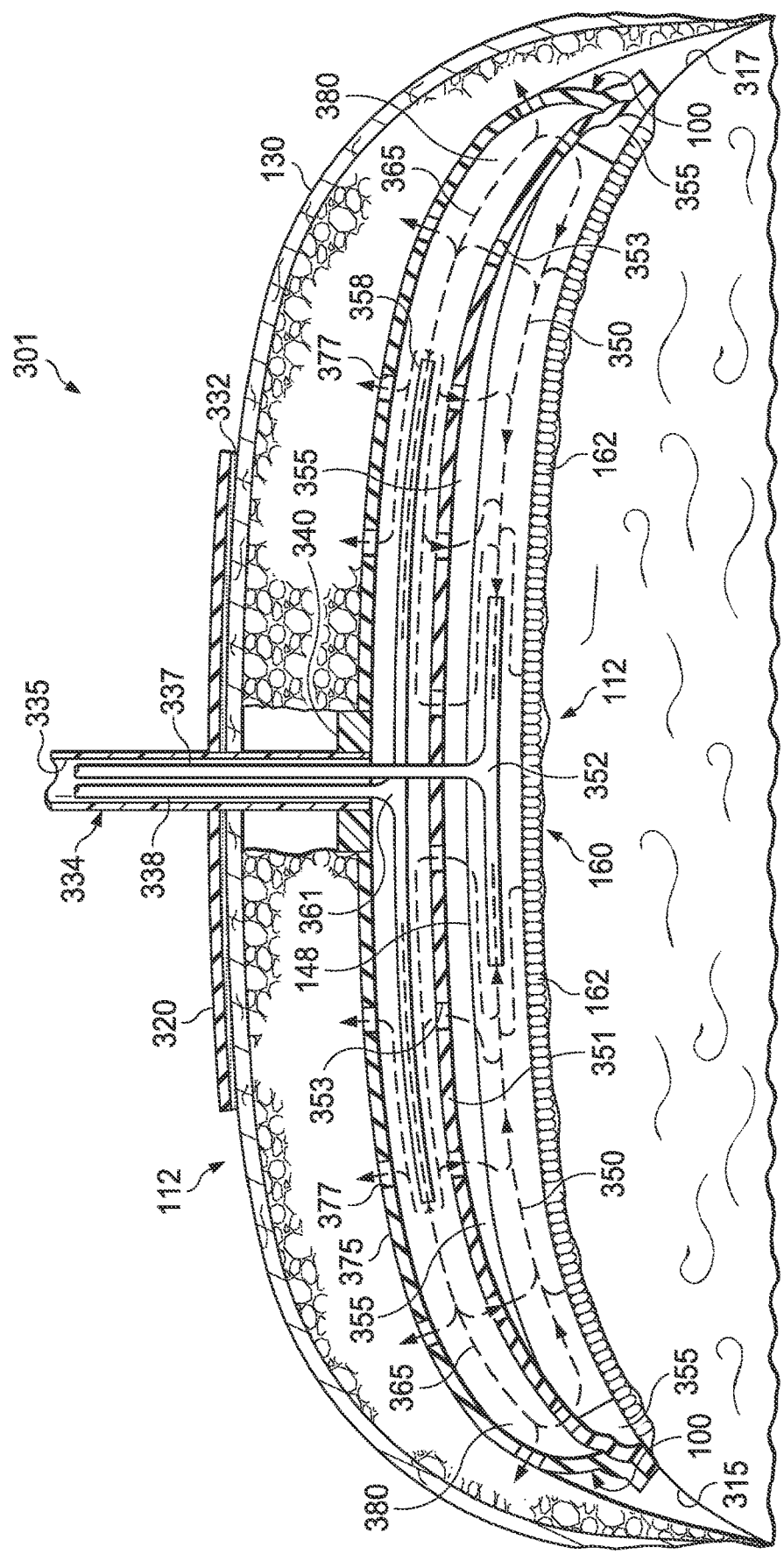
FIG. 5 is a schematic diagram, with a portion in cross-section, of an illustrative device containing a dressing with an integral wound filler sheet for treating an abdominal cavity that may be associated with some embodiments of the therapy system of FIG. 3.

Alternatively, as shown in FIG. 5, the optional fluid instillation system can be integral with but separate from the application of negative pressure for fluid collection. In some therapy embodiments, negative pressure can be applied at the same time as fluid is instilled, meaning that fluid withdrawal pathways and fluid supply pathways may need to be separated. For example, in FIG. 5, negative pressure can be applied to tissue site 112 by negative-pressure source 306 through fluid removal pathways in the manifolding layer 148 in chamber 355 and through fluid withdrawal lumen 337 into a container, such as container 310. Fluid or medicament can simultaneously be provided by fluid source 308 through fluid supply lumen 338 and through fluid supply pathways via a plurality of fluid delivery tubes 358 in chamber 380. Although treatment device 301 may be adapted to simultaneously provide fluid or medicament with negative pressure, it is still contemplated that the therapy system 300 shown in FIG. 5 may be operated to alternate application of negative pressure and instillation of fluid, as desired.

In the example of FIG. 5, the fluid delivery tubes 358 and optional distribution hub 361 may be considered components of an instillation matrix and may be constructed of a variety of different materials, such as soft medical-grade silicone or PVC tubing material. The plurality of fluid delivery tubes 358 may vary in size, based on the particular size and application of the treatment device 301, as well as the conditions of the tissue site 112 to which the treatment device 301 is to be applied. For example, the fluid delivery tubes 358 may have an inner diameter of between 0.5 mm and 4 mm. In some embodiments, the fluid delivery tubes 358 may have an inner diameter of between 1 mm and 2 mm. The rather small size of the fluid delivery tubes 358 may be conducive for avoiding patient discomfort during therapy as well as ease of removal of the treatment device 301 following completion of therapy.

In some embodiments, the fluid removal tubes may additionally function to communicate negative pressure and draw fluids through both the ends as well as along the lengths of the fluid removal tubes. For example, some embodiments of the fluid removal tubes connected to fluid removal hub 352 may include open ends as well as openings or apertures, such as removal pathway apertures, along the length of the fluid removal tubes. In some embodiments, the fluid delivery tubes 358 may only have open ends, such as delivery ends, and may otherwise be fluidly isolated from the surroundings along the length of the fluid delivery tubes 358. In some embodiments, the treatment device 301 may be offered in a single size with the option to cut and remove portions of the treatment device 301 to reduce its size, thus potentially shortening the length of the fluid delivery tubes 358, as required on an individual patient basis. By having openings of the fluid delivery tubes 358 only at the ends of the individual tubes, greater levels of customization may be achieved since the fluid delivery tubes or instillation matrix do not rely on a set length of the fluid delivery tubes 358 or number or size of perforations along the fluid delivery tubes 358 to evenly distribute instillation fluid. In other embodiments, the fluid delivery tubes 358 may exhibit a plurality of perforations to enable more even distribution of instillation fluid across the chamber 355 and amongst the tissue site 112. In still other embodiments, rather than having open ends for delivering instillation fluid to a tissue site, each of the fluid delivery tubes 358 may instead have closed ends, such as delivery tube closed ends, and thus may include openings or perforations, such as delivery tube perforations. The fluid delivery tubes 358 may include both open ends as well as perforations along their lengths, should the particular need or application arise.

The fluid delivery tubes 358, as well as any other components of an instillation matrix, may be adapted to deliver fluids across the tissue site 112 in a substantially uniform manner. For example, each of the fluid delivery tubes 358, the delivery ends, and the delivery tube perforations may be adapted to provide substantially the same back-pressure. Such a configuration may prevent fluid from traveling more freely through or otherwise favoring one or more of the fluid delivery tubes 358 over another one or more of the fluid delivery tubes 358. Herein, back-pressure may refer to an increase in localized pressure caused by a resistance to fluid flow, such as through the confined space of a lumen or aperture. Back-pressure may result from the geometric configuration and material properties of the confined space, such as, without limitation, the size of the space, the presence and shape of bends or joints in the space, surface finishes within the space, and other characteristics. In some embodiments, a fluid hub, such as distribution hub 361, may not be necessary if the perforations along the lengths of the fluid delivery tubes 358 are sized to provide a substantially even distribution of fluid throughout the tissue site 112. Consistency among the size and configuration of the fluid delivery tubes 358, and the number and size of the delivery ends and delivery tube perforations in each of the fluid delivery tubes 358, for example, may enhance the uniformity of fluid delivery to the tissue site 112.

In some embodiments, the fluid delivery tubes 358 may have a cylindrical tube shape and may have an internal diameter between about 2 millimeters and about 6 millimeters. In some other embodiments, the fluid delivery tubes 358 may have an alternate tubing profile, where a lower-profile, or "flatter" tubing profile may be used to increase user comfort when the treatment device 301 is in place in a tissue site 112. The delivery apertures, in some embodiments, may have a diameter between about 0.1 millimeters and about 0.8 millimeters. Sizing the internal diameter or cross-section of the fluid delivery tubes 358 substantially larger than the size, cross-section, or diameter of the delivery ends and the delivery tube perforations may provide a substantially uniform pressure within each of the fluid delivery tubes 358. In such an embodiment, fluid flow velocity within the fluid delivery tubes 358 may be relatively low or substantially static in comparison to the relatively high fluid flow velocity through the delivery apertures.

Although not shown in the accompanying figures, in some embodiments, the fluid delivery tubes 358 may be arranged in the form of a grid, for example extending outward from a central distribution hub 361, such as radially, with tubing segments that fluidly connect each of the outwardly-extending fluid delivery tubes 358. Perforations may exist along any or all portions of the outwardly-extending fluid delivery tubes 358, as well as the connecting tubing segments, in such embodiments.

In some embodiments, such as shown in FIG. 5, the treatment device 301 may comprise a distribution material for assisting with distributing the installation fluid, such as filler material 340, as a complement to or an element of the distribution hub 361. Whether the distribution hub is elongate, cylindrical in shape, or bell-shaped, or comprises a fitting, such as a tube, tubular fitting, pipe, barbed connection, or similar structure, the distribution hub 361 or filler material 340 may generally be configured to be fluidly coupled between the fluid supply lumen 338 of the conduit 334 and the fluid delivery tubes 358.

In some embodiments, such as shown in FIG. 5, the second liquid-impermeable layer 375 may be disposed atop first liquid-impermeable layer 351 on a surface facing opposite from the manifolding layer 148. In this configuration, the first liquid-impermeable layer 351 and the second liquid-impermeable layer 375 may be coupled at their edges, defining chamber 380 between. In some embodiments, each of the liquid-impermeable layers may be formed from a polyurethane material, for example each having a thickness of between 25 μm and 500 μm.

Referring primarily to FIG. 5, the treatment device 301 may be adapted to provide negative pressure from the negative-pressure source 306 of the therapy unit 304 to a tissue site 112, such as an abdominal cavity, and to collect and transport fluid extracted from the tissue site 112. Additionally, the treatment device 301 may also be adapted to deliver a fluid, such as a treatment fluid or medicament, from the fluid source 308 of the therapy unit 304 to the tissue site 112. In some embodiments, the dressing 100 may include multiple liquid-impermeable layers, or visceral protective layers, which protect the underlying abdominal contents of the tissue site 112. For example, in some embodiments, the dressing 100 may include a first liquid-impermeable layer 351 having fenestrations 353. In addition, in embodiments having simultaneous capability to provide negative pressure and fluid instillation, the dressing 100 may include a second liquid-impermeable layer 375. Though shown in FIG. 5 as containing fenestrations 353 for promoting fluid removal throughout an abdominal cavity, the first liquid-impermeable layer 351 may contain fenestrations only at the outer edges of the layer(s) or may contain no fenestrations. Similarly, though shown in FIG. 5 as having a plurality of fenestrations 377, the second liquid-impermeable layer 375 may alternatively exhibit fenestrations only at the outer edges of the second liquid-impermeable layer 375 or no fenestrations at all, thereby partially or totally allowing for the installation liquid to take a circuitous path out of the chamber 380 through fenestrations 377, among the abdominal contents, around the dressing 100, back in through the assembly of manifolding layer 148 and filler layer 160, optionally into chamber 355, and through the fluid removal pathways 350 into the fluid removal tubes toward the fluid removal hub 352.

Referring again to FIG. 5, an interface may provide both a negative-pressure connection as well as a fluid supply connection to the treatment device 301. The interface may be sized, shaped, or otherwise adapted to fluidly connect a negative-pressure lumen 335 and a fluid withdrawal lumen 337 of the conduit 334, as well as a separate fluid supply lumen 338 if desired, to the treatment device 301 in any suitable manner. In some embodiments, the interface may fluidly couple the negative-pressure lumen 335 and the fluid supply lumen 338 through the cover 320. For example, one or more sealing member apertures may be disposed through the cover 320 to provide fluid communication and access to the components of the treatment device 301 positioned within a sealed space involving the tissue site 112.

In some embodiments, the interface may be a multi-port interface providing both the negative-pressure connection and the fluid supply connection as individual, fluidly isolated ports within the multi-port interface, such as conduit 334. In such an embodiment, a wall of one of the individual lumens, such as the fluid withdrawal lumen 337 or the fluid supply lumen 338, may be coupled to the filler material 340 or to the distribution hub 361 for fluidly isolating the fluid supply connection from the negative-pressure connection. Other configurations for maintaining the fluid isolation of the negative-pressure lumen 335 from the fluid supply lumen 338 are possible.

FIG. 5 shows an exemplary embodiment in which fluid instillation pathways 365 emanating from distribution hub 361 through fluid instillation tubes 358 and are separate from fluid removal pathways 350 flowing into manifolding layer 148 through fluid removal tubes and fluid removal hub 352. The configuration of providing the instillation fluid and the associated back-pressure along the fluid instillation pathways 365 through fluid instillation tubes 358 and using the distribution hub 361 may facilitate delivery of the instillation fluid to the tissue site 112 in a substantially uniform manner.

The treatment device 301 may be covered at the tissue site 112 with the cover 320 to provide a sealed space containing the treatment device 301. The cover 320 may be positioned and fluidly sealed about the tissue site 112 with the attachment device 332, as described above. Apertures in the cover 320 may be cut or otherwise disposed through the cover 320 as necessary, if not already provided as part of the cover 320. In some embodiments, instillation fluid may be independently fed from a fluid source, such as fluid source 308, through the fluid supply lumen 338 and into the chamber 380. Thus, in some embodiments such as shown in FIG. 5, the instillation fluid may be fed directly to a fluid hub, such as distribution hub 361, and therefore, the fluid instillation pathways 365 and the fluid removal pathways 350 may be controlled as separate entities. In these embodiments, potential contamination of clean fluid instillation pathways may be reduced or largely eliminated, and a more efficient cleansing cycle may be obtained. In other embodiments such as shown in FIG. 4, the instillation fluid may also be fed directly into a fluid hub and through fluid distribution pathways, but a single hub and a single set of pathways would function for both fluid instillation and fluid removal. In those embodiments, fluid removal hub 352 in FIG. 4 would function to assist fluid removal under negative-pressure conditions and to assist fluid instillation under conditions for flowing fluid to tissue site 112; similarly, fluid removal pathways 350 in FIG. 4 would function in the arrow directions to assist fluid removal under negative-pressure conditions and opposite from the arrow directions to assist fluid instillation under conditions for flowing fluid to tissue site 112. Depending on how the components of the treatment device 301 are specifically configured, in some embodiments such as shown in FIG. 5, fluid may be fed through the fluid instillation tubes 358 directly into low points of an abdomen, such as the paracolic gutters 315 and 317.

Activating the negative-pressure source 306 may provide negative pressure to the negative-pressure lumen 335 of the conduit 334, to the manifolding layer 148 through the fluid withdrawal lumen 337, and into chamber 355. The fluid source 308 may provide instillation fluid to the chamber 380 through the fluid supply lumen 338 (or to the chamber 355 through repurposed fluid removal lumen 337, such as in FIG. 4), for example, by activating a pump or positive-pressure source in the fluid source 308, or by operation of gravitational or manual user forces acting on the instillation fluid. Negative pressure and instillation fluid may be provided to the treatment device 301 simultaneously, or cyclically, at alternate times. Further, negative pressure and instillation fluid may be applied to the treatment device 301 intermittently or continuously.

When the negative-pressure source 306 is activated, the fluid removal lumen 337 of the conduit 334 may distribute the negative pressure to the manifolding layer 148 or optionally to the fluid removal hub 352 in fluid communication therewith. Fluid from the tissue site 112 may be drawn or extracted through the open ends and removal pathway apertures into the fluid removal pathways 350. Fluid may be moved through the fluid removal pathways 350 and optionally into fluid removal hub 352, where the fluid may be drawn into the fluid withdrawal lumen 337 of the conduit 334 and ultimately the container 310.

In some embodiments, some portion of fluid extracted from the tissue site 112 may be stored within the manifolding layer 148 of the treatment device 301 before being drawn into the fluid withdrawal lumen 337. The capability to provide fluid storage and permeability while under negative pressure may require the manifolding layer 148, or other porous portion of the assembly or of the dressing layer 110, to have a higher volume of fluid capacity compared to that of the fluid delivery tubes 358 that may be under positive pressure. Fluid being instilled or delivered to the tissue site 112, for example through fluid delivery tubes 358, may not be required to first pass through portions of the treatment device 301, such as the manifolding layer 148, that may encompass a larger volume. Such a configuration is shown in FIG. 5 and may enhance the distribution and efficient use of the instillation fluid. Following completion of negative-pressure and/or fluid instillation therapy, a user may remove the treatment device 301 as a largely intact structure, thus maintaining an ease of use of the treatment device 301.

In some embodiments, the fluid delivery tubes 358 may comprise polyurethane film or foam bags with perforations. For example, the fluid delivery tubes 358 may be constructed using two layers of polyurethane film of approximately 100 micrometers in thickness that are edge-welded together. The fluid delivery tubes 358 may have open ends for targeted fluid delivery. In some embodiments, within each of the fluid delivery tubes 358 and the optional fluid removal hub 352 may be a central core adapted to ensure that an open pathway is maintained and to aid a user with handling during placement. For example, this central core may be an open-cell foam, such as a reticulated polyurethane. Dimensions of the central core material positioned within the fluid delivery tubes 358 may vary; for example, the central core material may range from around 2 mm to 10 mm in thickness by about 5 mm to 15 mm in width. In some embodiments, the central core material may be around 6 mm in thickness by 10 mm in width. The length of the central core material may be varied based on overall sizing considerations of the treatment device 301. Some embodiments may include a central core material having a width that varies along its length, which may allow for break points to provide user customization and sizing. In some instances, the fluid delivery tubes 358 may be adapted so that any instillation fluid remaining within the fluid delivery tubes 358 following delivery of instillation fluid by the fluid source 308 may be squeezed from the fluid delivery tubes 358 when negative pressure is applied to the treatment device 301, thus ensuring that substantially all instillation fluid is emptied from the fluid delivery tubes 358 to better regulate the volume of instillation fluid provided during therapy cycles.

In some embodiments, fluid instillation may optionally incorporate a layer of manifolding material or matrix, which may be referred to as an optional instillation matrix. In FIG. 4, the manifolding layer 148 may serve that purpose, when not being used for fluid removal. In FIG. 5, the optional instillation matrix could surround the fluid delivery tubes 358 emanating from distribution hub 361 and be oriented between the second liquid-impermeable layer 375 and the first liquid-impermeable layer 351 in chamber 380. If present, the optional instillation matrix could help ensure that the fluid instillation pathway remains open and not occluded or sealed when subjected to negative pressure. Example materials for the optional instillation matrix may be similar to those for the manifolding layer 148 and may include foams, such as polyurethane foam, Libeltex TDL2, Libeltex TL4, Baltex 3DXD spacer fabrics, Baltex 4DXD spacer fabrics, embossed films, or some other formed structure.

In some additional methods for providing negative-pressure therapy and fluid instillation to a tissue site, rather than an automated or other form of mechanical instillation device, a manually-controlled instillation vessel, such as a fluid bag, bottle, or other vessel, may be incorporated. Thus, in some embodiments, during a first stage of a therapy cycle, a negative-pressure source may apply negative-pressure therapy to a treatment device and tissue site, while a device such as a clamp, valve, or other form of closure device may prevent fluid from being communicated from the manually-controlled instillation vessel to the treatment device and tissue site. In some embodiments, during a subsequent stage of a therapy cycle, a user may open the clamp or other form of closure device and may manually regulate the volume of fluid being instilled. During this instillation phase, the negative-pressure source may remain active, thus providing immediate removal of the instilled fluid from the treatment device and tissue site. Thus, there may be virtually no dwell time of the fluid in the tissue site, according to some embodiments of the method. The user may then re-clamp or otherwise close the closure device, thus stopping the flow of instillation fluid from the manually-controlled instillation vessel. The negative-pressure source may then continue to remove excess or remaining instillation fluid, as well as exudates, from the treatment device and tissue site. In some other embodiments of the disclosed method, rather than allowing the negative-pressure source to remain active while the fluid is instilled from the manually-controlled instillation vessel, the negative-pressure source may be paused, thus allowing the instillation fluid to dwell in the tissue site for a prescribed period of time. When appropriate, the user may close off the manually-controlled instillation vessel from delivering instillation fluid. Prior or subsequent to instillation being stopped, negative-pressure therapy may be recommenced, during which time any excess or remaining fluids may be removed from the treatment device and tissue site. In some embodiments, the negative-pressure source may remain active, while instillation fluid may be periodically provided in various stages.

The systems, apparatuses, and methods described herein may provide significant advantages. For example, some embodiments of the treatment device 301 may provide a combined temporary abdominal closure dressing system with fluid instillation capability through an independent matrix of fluid delivery tubing, as well as negative-pressure fluid removal pathways for removal of contaminated fluid. Some embodiments may provide means for irrigating and cleansing an abdominal cavity while supporting and protecting the abdominal contents, as well as increasing interstitial fluid flow, removing contaminated fluid, and controlling and/or reducing edema. Additionally, as a result of the various layers and components of the dressing 100 applying tension and closing force to the abdominal contents, quicker primary fascia closure of the abdominal cavity may be facilitated.

In some embodiments, the therapy system 300 may provide means for irrigating all areas of an abdominal cavity, including small bowel loops, gutters, retroperitoneal space, portions of the lymphatic system, etc., all while the dressing system is in place, advantageously reducing time required for patients and clinical staff in the operating room. Various embodiments can offer configurations of fluid pathways designed to maximize the exposure of internal organs of abdominal tissue sites to fluid instillation therapy. Other embodiments of instillation besides those shown are additionally or alternatively possible. Some embodiments may also allow for longer dressing application times without adhering to the fascia of abdominal tissue sites. In some embodiments, repeatable as well as reliable fluid instillation that may be provided relatively evenly to various portions of a tissue site. In some embodiments, fluid irrigation and cleansing may be relatively consistent, advantageously leading to a reduction in mortality of patients suffering from septic abdominal cavities. Fluid instillation may be managed at a patient's bedside and may be custom-tailored and adjusted on a case-by-case basis.

Use of the therapy system 300 may enable exudate and infectious material to be drained from tissue sites, such as the abdominal cavity, which can reduce the presence of contaminated abdominal fluids to promote healing. Furthermore, the therapy system 300 may provide separate instillation and negative-pressure pathways to ensure that contaminated fluid is fully removed from the tissue site 112. In some embodiments of the therapy system 300, instillation fluid may not be recirculated back into the tissue site, which can increase the clinical benefits of irrigating tissue sites.

The design of the therapy system 300 or specific portions thereof may also allow for user sizing and/or customization at the time of application to a patient in the operating room. In some embodiments, improved ease of use for dressing placement, sizing, and removal may be provided by built-in sizing or placement visual markings or indicators for guiding users. Some embodiments of the disclosed dressing systems may also include various components, such as the fluid instillation pathways and/or fluid removal pathways already pre-attached to the structural dressing layers to further streamline and simplify use. In some embodiments, not only may improved fluid delivery and removal be enabled, as compared to existing dressing systems, but increased ease of use may be promoted.

In some embodiments, the therapy system 300, and particularly one or more layers or portions of the dressing 100, may optionally comprise one or more additional materials. Such optional components may include, for example, active materials such as preservatives, stabilizing agents, plasticizers, matrix strengthening materials, dyestuffs, and combinations thereof.

Additionally or alternatively, the description includes one or more of the following embodiments.

Embodiment 1. An apparatus for filling a wound, the apparatus comprising: an array of at least four truncated ellipsoids interconnected to define at least one fluid path through the array; wherein the interconnected ellipsoids are comprised of a polyolefin, a polyester, a polyamide, a polystyrene, a polydiolefin, a polyacrylonitrile, a polysiloxane, or a copolymer or combination thereof; and wherein each of the interconnected ellipsoids has a surface hardness from about 0 Shore A to about 25 Shore A.

Embodiment 2. An apparatus for filling a wound, the apparatus comprising: an array of interconnected polymeric ovules having a truncated ellipsoidal shape, wherein: each set of four interconnected ovules defines a fluid pathway extending perpendicularly through the array; each truncated ellipsoidal shape comprises an approximately elliptical contact surface at each contact surface between two interconnected ovules; and each interconnected polymeric ovule has its longest principal axis oriented substantially perpendicular to the array.

Embodiment 3. An apparatus for filling a wound, the apparatus comprising: a layer having a plurality of fluid pathways through the layer from a first surface to a second surface, wherein: an array of connected polymeric protrusions extends through the layer connecting the first and second surfaces; each set of four connected polymeric protrusions from each of the first and second surfaces defines one fluid pathway extending perpendicularly through the array; and each fluid pathway has four continuously-curved concave sides and has a parallelogram-shaped cross-section with continuously-curved concave edges.

Embodiment 4. The apparatus of embodiment 3, wherein the polymeric protrusions have a shape of truncated ellipsoids, optionally of truncated spheroids.

Embodiment 5. The apparatus of embodiment 1 or embodiment 4, wherein each of the truncated ellipsoids, optionally the truncated spheroids, has a principal axis oriented substantially perpendicular to the array.

Embodiment 6. The apparatus of embodiment 4 of embodiment 5, wherein the interconnected ellipsoids (or spheroids) are truncated only at each surface where the ellipsoids (or spheroids) are interconnected.

Embodiment 7. The apparatus of any of the previous embodiments, wherein the array comprises: at least three columns comprising two edge columns and at least one central column; and at least three rows comprising two edge rows and at least one central row, and wherein each set of four interconnected ovules or truncated ellipsoids (or truncated spheroids) is arranged in two of the at least three rows and two of the at least three columns.

Embodiment 8. The apparatus of embodiment 7, wherein the array comprises four corner ovules, at least four edge ovules, at least one central ovule, and at least four fluid pathways interstitially therebetween, each central ovule having a truncated ellipsoidal (or spheroidal) shape with four elliptical contact surfaces, each edge ovule having a truncated ellipsoidal (or spheroidal) shape with three elliptical contact surfaces, and each corner ovule having a truncated ellipsoidal (or spheroidal) shape with two elliptical contact surfaces.

Embodiment 9. The apparatus of any one of embodiments 2-8, wherein the interconnected ovules are comprised of a polyolefin, a polyester, a polyamide, a polystyrene, a polydiolefin, a polyacrylonitrile, a polysiloxane, or a copolymer or combination thereof.

Embodiment 10. The apparatus of any of the previous embodiments, wherein each interconnected ovule or ellipsoid (or spheroid) has its two principal axes other than the longest principal axis, respectively, oriented at approximately a 45° angle to a row direction of the array and at approximately a 45° angle to a column direction of the array.

Embodiment 11. The apparatus of any one of the previous embodiments, wherein the array of interconnected ellipsoids (or spheroids) or interconnected ovules has an upper surface and a lower surface, and wherein the upper surface or the lower surface or both has a hardness from about 0 Shore A to about 25 Shore A.

Embodiment 12. The apparatus of embodiment 11, wherein: the upper surface or the lower surface or both has a coating disposed thereon that exhibits a hardness of at least 55 Shore A; the coating is comprised of a cellulosic material, a polyester, a polyamide, a polycarbonate, a perhalogenated polyolefin, an aramid, a polybenzimidazole, a polysulfone, or a copolymer, combination, or cross-linked gel thereof; or both.

Embodiment 13. The apparatus of any of the previous embodiments, wherein at least a portion of the interconnected ellipsoids (or spheroids) or at least a portion of the interconnected ovules comprise one or more grooves on an outer surface of each ellipsoid (or spheroid) or of each ovule that extend at least partially in a direction of its longest principal axis.

Embodiment 14. The apparatus of embodiment 13, wherein each groove has an average depth no more than 30% of a diameter of each interconnected ovule or of each interconnected ellipsoid (or spheroid) along a principal axis direction other than the longest principal axis.

Embodiment 15. The apparatus of any of the previous embodiments, wherein a longest principal axis of each interconnected ellipsoid (or spheroid) or each interconnected ovule is from about 3 mm to about 6 mm or is from about 2 mm to about 4 mm.

Embodiment 16. The apparatus of any of the previous embodiments, wherein each fluid pathway has a minimum width dimension from about 500 microns to about 1500 microns.

Embodiment 17. The apparatus of any of the previous embodiments, wherein the apparatus is translucent.

Embodiment 18. The apparatus of any of the previous embodiments, further comprising a wound healing agent in or on the array, the wound healing agent comprising a non-steroidal anti-inflammatory drug, a steroid, an anti-inflammatory cytokine, an anaesthetic, an antiseptic, an antimicrobial agent, a growth factor, a peptide, a microRNA, an antioxidant, or a combination thereof, optionally wherein the antimicrobial agent comprises silver, a silver salt, a tetracycline, a beta-lactam, a macrolide, an aminoglycoside, a fluoroquinolone, a cellulose ethyl sulfonate, or a combination thereof.

Embodiment 19. A dressing for treating a tissue site, the dressing comprising: an apparatus according to any of the previous embodiments; a dressing layer coupled to the apparatus; a backing layer disposed over a surface of the dressing layer opposite from the apparatus; and an attachment device disposed on at least a margin of the backing layer.

Embodiment 20. The dressing of embodiment 19, wherein the attachment device is configured to form a seal with a tissue site, and wherein the dressing layer is coupled to the apparatus on a surface opposite the protrusions, or on a surface formed by truncation of the ovules or of the ellipsoids on one end of a principal axis oriented substantially perpendicular to the array.

Embodiment 21. The dressing of embodiment 19 or embodiment 20, wherein the dressing layer comprises an absorbent layer containing from about 45% to about 90% carboxymethyl cellulose fibers and from about 10% to about 55% reinforcing fibers.

Embodiment 22. The dressing of any of embodiments 19-21, wherein the dressing layer comprises a manifolding layer configured to allow both fluid removal and fluid instillation therethrough.

Embodiment 23. A system for treating a tissue site with negative pressure, the system comprising: an apparatus according to any of embodiments 1-18 or a dressing according to any of embodiments 19-22; a negative-pressure source fluidly coupled to the dressing and configured to enable fluid removal through the dressing; optionally a negative-pressure conduit; optionally a negative-pressure connector subsystem for fluidly coupling the negative-pressure source to the apparatus or the dressing for fluid removal; and optionally a container fluidly coupled to the negative-pressure source and to the apparatus or to the dressing and adapted to collect fluid.

Embodiment 24. A method for treating a compartmented wound site, for example comprising a peritoneal or abdominal cavity, the method comprising: deploying within a compartmented wound site the apparatus of any of embodiments 1-18 or a dressing according to any of embodiments 19-22, or at least a portion of the system for treating a tissue site according to embodiment 23; deploying a negative-pressure connector subsystem; deploying a sealing member to form a fluid seal over the open cavity; fluidly coupling the negative-pressure connector subsystem to a negative-pressure source; and activating the negative-pressure source.

Embodiment 25. A method for treating a surface wound site, for example comprising a burn, a graft, an overhang wound, a contusion, or a post-operative wound, the method comprising: deploying over the surface wound site the apparatus of any of embodiments 1-18 or a dressing according to any of embodiments 19-22, or at least a portion of the system for treating a tissue site according to embodiment 23; deploying a negative-pressure connector subsystem; deploying a sealing member to form a fluid seal over the surface wound site; fluidly coupling the negative-pressure connector subsystem to a negative-pressure source; and activating the negative-pressure source.

Embodiment 26. A method for treating a tunnel wound site, for example comprising a puncture or a fistula, the method comprising: deploying within the tunnel wound site the apparatus of any of embodiments 1-18 or a dressing according to any of embodiments 19-22, or at least a portion of the system for treating a tissue site according to embodiment 23, the dressing substrate comprising a cylinder or tube; deploying a negative-pressure connector subsystem; deploying a sealing member to form a fluid seal over the tunnel wound; fluidly coupling the negative-pressure connector subsystem to a negative-pressure source; and activating the negative-pressure source.

Embodiment 27. A method of reducing edema and/or increasing interstitial fluid flow for a tissue site, the method comprising positioning the apparatus of any of embodiments 1-18 or a dressing according to any of embodiments 19-22, or at least a portion of the system for treating a tissue site according to embodiment 23 over the tissue site.

EXAMPLES

One, some, or all of the advantages associated with the disclosed compositions, dressings, methods of making, and methods of using or treating may be further demonstrated by the following non-limiting examples.

Example 1

In this Example, a non-GLP histopathological study was conducted to evaluate performance in full-thickness skin excisional wounds in porcine animals using wound filler materials with negative-pressure wound therapy (NPWT). Each full-thickness skin excisional wound was approximately 3 cm×7.5 cm, with each sample wound filler material being approximately the same size as each wound. Each sample wound filler material was placed within its respective full-thickness skin excisional wound, topped with a polyurethane drape to form a dressing, and used in conjunction with a T.R.A.C.™ Pad negative-pressure interface to enable V.A.C.™ Therapy (available from KCI of San Antonio, TX). Each wound was treated in this way for about a six (6) day testing period, with en bloc wound sites, including adequate surrounding tissue, being excised for histopathological evaluation. After excision, each wound site was affixed to a substrate and submerged in 10% neutral buffered formalin (NBF) for about 72 hours, after which affixed wound sites were transferred to alcohol (70% ethanol) until being removed for analysis. After removal, wound sites were trimmed, processed, embedded in paraffin, sliced in cross-section (approximately 5 microns thick), and stained with hematoxylin and eosin (H&E) for contrast. Two protocols were conducted for each wound: Group 1 wounds included a dressing change at the midpoint of the experiment (Day 3), such that each fresh dressing was only in contact with its respective wound site for ~3 days; and Group 2 wounds had the original dressing maintained for the entire ~6 days.

Sample 1 corresponded to a wound filler material according to FIGS. 1A-1E and having top and bottom surfaces each with a Shore A hardness of approximately 0. Sample 2 corresponded to a wound filler material according to FIGS. 1A-1E and having top and bottom surfaces each with a Shore A hardness of approximately 7. Comparative Sample 3 corresponded to a GranuFoam™ wound filler material (available from KCI of San Antonio, TX). Comparative Sample 4 corresponded to a standard gauze wound filler material.

Total wound site granulation and tissue ingrowth were probed for each sample. Wound site granulation was evaluated quantitatively for each excised wound site using ImagePro Plus™ software. Granulation tissue limits of both underlying granulation tissue filling each wound bed and (granulation) tissue ingrowth into each wound filler/dressing material were marked digitally on images of each wound bed cross-section. Wound section granulation tissue thickness measurements were made approximately 2 mm from the left edge of each wound and were repeated approximately every 2 mm until the last measurement approximately 2 mm from the right edge of each wound. Measurements were made approximately perpendicular to the contour of the tissue underlying each wound. Where granulation tissue at a measurement point was not continuous for its full depth (for example, where interrupted by seroma or other non-granulation tissue feature), individual measurements were taken and added to calculate a sum representing the underlying granulation tissue thickness. Total granulation tissue thickness represented the sum of the underlying granulation tissue thickness and the tissue ingrowth thickness. Underlying granulation tissue was also evaluated semi-quantitatively, according to the following scoring scale: 0=no observable granulation filling a wound bed; 1=~1% to ~25% of a wound bed is filled with granulation tissue; 2=~26% to ~50% of a wound bed is filled with granulation tissue; 3=~51% to ~75% of a wound bed is filled with granulation tissue; 4=~76% to ~100% of a wound bed is filled with granulation tissue; and 5=more than 100% of a wound bed is filled with granulation tissue (excessive granulation tissue). Amount of granulation tissue ingrowth into each wound filler/dressing material was also evaluated semi-quantitatively, according to the following scoring scale: 0=absent; 1=minimal; 2=mild' 3=moderate; 4=marked; and 5=severe. The results are shown in Table 1 below.

It can be seen from the tabulated results, both quantitatively and in semi-quantitative scoring, that wound filler Samples 1 and 2 exhibited slightly lower mean total granulation tissue thickness, and notably also lower mean tissue ingrowth thickness, in both experimental groups of negative-pressure wound treatments than Comparative wound filler Samples 1 and 2. Importantly, the most significant difference can be seen in the mean tissue ingrowth thickness in Group 1 NPWT tests, where semi-quantitative scoring showed a statistically significant reduction in tissue ingrowth scores for Samples 1 and 2, relative to Comparative Samples 3 and 4, and where quantitative mean tissue ingrowth thicknesses are on the edge of statistical significance. Furthermore, the ratio of tissue ingrowth to wound bed granulation tissue is desirably low for Samples 1 and 2, as it can be highly desirable to reduce tissue ingrowth while simultaneously promoting wound bed granulation, which implies wound healing. For Samples 1 and 2, slight increase in mean tissue ingrowth thicknesses and scores while maintaining similar mean total granulation tissue thicknesses in Group 2 NPWT tests, as well as an increased ratio of tissue ingrowth to wound bed granulation tissue in Group 2 NPWT tests. These results appear to imply that, for wound filler Samples 1 and 2 under NPWT therapy, granulation was stimulated in the wound bed on the relatively short time scale of ~3 days or less and that little if any additional granulation was stimulated on the subsequent time scale of ~3 additional days. Additionally, these results appear to imply that, for wound filler Samples 1 and 2 under NPWT therapy, wound bed granulation likely did not reduce between ~3 days and ~6 days but more likely wound bed granulation appeared to turn into tissue ingrowth. This latter observation would appear to indicate that, for apparatuses or dressings according to FIGS. 1A-1E, an advantageous combination of significant healing wound bed granulation and significantly little or no tissue ingrowth can be attained by NPWT therapy involving periodic dressing changes and that such an advantage can recede with increased time between dressing changes. The biological or physico-chemical reasons behind these histopathological observations and implications are not currently clear, and there can be varying theories which are not presented here.

TABLE 1

| Label (Test) | Mean total granulation tissue thickness (mm) | Granulation tissue filling wound score | Mean underlying granulation tissue thickness (mm) | Mean tissue ingrowth thickness (mm) | Granulation tissue ingrowth score |
|---|---|---|---|---|---|
| Sample 1 (Grp 1) | 0.9 ± 1.0 | 1.5 ± 0.7 | 0.8 ± 0.8 | 0.1 ± 0.1 | 0.5 ± 0.7 |
| Sample 2 (Grp 1) | 1.1 ± 0.6 | 1.5 ± 0.7 | 0.7 ± 0.6 | 0.4 ± 0.0 | 1.0 ± 0.0 |
| Comparative Sample 3 (Grp 1) | 1.5 ± 0.4 | 2.0 ± 0.0 | 0.7 ± 0.1 | 0.8 ± 0.4 | 2.0 ± 0.0 |
| Comparative Sample 4 (Grp 1) | 2.7 ± 1.3 | 3.0 ± 0.0 | 2.1 ± 0.9 | 0.7 ± 0.4 | 2.0 ± 0.0 |
| Sample 1 (Grp 2) | 0.7 ± 0.5 | 1.3 ± 0.5 | 0.4 ± 0.4 | 0.3 ± 0.2 | 1.0 ± 0.0 |
| Sample 2 (Grp 2) | 1.5 ± 2.1 | 1.3 ± 0.5 | 1.4 ± 2.2 | 0.2 ± 0.2 | 0.5 ± 0.6 |
| Comparative Sample 3 (Grp 2) | 1.6 ± 0.7 | 1.7 ± 0.6 | 0.9 ± 0.6 | 0.6 ± 0.3 | 1.7 ± 0.6 |
| Comparative Sample 4 (Grp 2) | 1.7 ± 0.4 | 2.0 ± 0.0 | 1.0 ± 0.2 | 0.6 ± 0.3 | 2.0 ± 0.0 |

Although not specifically tabulated herein, peel test studies were done on both Samples 1 and 2 and Comparative Samples 3 and 4 to probe ease of removal from each wound site at each dressing change. No significant difference was observed between peel tests at ~3 days and at ~6 days for Samples 1 and 2, and no significant difference was observed between peel tests for wounds filled by Samples 1 or 2 and wounds filled by Comparative Samples 3 or 4.

Non-Limiting Discussion of Terminology

While shown in a few illustrative embodiments and examples, a person having ordinary skill in the art will recognize that the systems, apparatuses, and methods described herein are susceptible to various changes and modifications and are not intended to limit the scope of the claimed subject matter. Moreover, recitation of multiple embodiments having stated features does not exclude other embodiments having additional features, or other embodiments incorporating different combinations of the stated features. Components may also be combined or eliminated in various configurations for purposes of sale, manufacture, assembly, or use. For example, in some configurations the treatment device 301 including the dressing 100, the container 310, or both may be eliminated or separated from other components for manufacture or sale. In other example configurations, the controller 309 may additionally or alternatively be manufactured, configured, assembled, or sold independently of other components. Specific examples are provided for illustrating how to make and use the compositions, and examples of methods are not intended to be a representation that given embodiments have, or have not, been made or tested. Equivalent changes, modifications and variations of some embodiments, materials, compositions and methods can be made within the scope of the appended claims, with substantially similar results.

As used herein, the words "include," "contain," and their variants, are intended to be non-limiting, such that recitation of items in a list is not necessarily to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments that do not contain those elements or features. Moreover, descriptions of various alternatives using terms such as "or" do not require mutual exclusivity unless clearly required by the context, and the indefinite articles "a" or "an" do not limit the subject to a single instance unless clearly required by the context.

Although the open-ended term "comprising," as a synonym of non-restrictive terms such as including, containing, or having, is used herein to describe example embodiments, embodiments may alternatively be described using more limiting terms such as "consisting of" or "consisting essentially of." Thus, for any given embodiment reciting materials, components or process steps with such open-ended terms, similar or analogous embodiments are contemplated consisting of, or consisting essentially of, such materials, components or processes excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

Disclosure of values and ranges of values for specific parameters, such as temperatures, molecular weights, weight percentages, etc., are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, disclosure of two or more ranges of values for a parameter, whether such ranges are nested, overlapping or distinct, may subsume all possible combination of ranges for the value that might be claimed using endpoints of the disclosed ranges. For example, if parameter X is exemplified herein to have values in the range of 1-10, or 2-9, or 3-8, Parameter X may be envisioned as having other ranges of values including 1-2, 1-3, 1-8, 1-9, 2-3, 2-8, 2-10, 3-9, 3-10, 8-9, 8-10, and 9-10.

The term "about," as used herein, is intended to refer to deviations in a numerical quantity that may result from various circumstances, for example, through measuring or handling procedures in the real world; through inadvertent error in such procedures; through differences in the manufacture, source, or purity of compositions or reagents; from computational or rounding procedures; and other deviations as will be apparent by those of skill in the art from the context of this disclosure. For example, unless otherwise defined by the specification per se or by the context of the specification, the term "about," with reference to a value, may refer to any number that would round to that value, based on a significant digit analysis. In such a circumstance, a value of "about 30%", assuming the "3" is the only significant digit, could encompass from 25% to just below 35%. However, the context of the specification would limit that interpretation based on significant digits, so that the "about" ranges do not overlap. For example, if the specification discloses ranges that include "about 25%, about 30%, about 35%," etc., about 30% in that context could encompass from 27.5% to just below 32.5%. Alternatively, the term "about" may refer to deviations that are greater or lesser than a stated value or range by ±10% of the stated value(s), as appropriate from the context of the disclosure. In such a circumstance, a value of "about 30%" may encompass from 27% to 33%. Whether or not modified by the term "about," quantitative values recited herein include equivalents to the recited values, for example, deviations from the numerical quantity, as would be recognized as equivalent by a person skilled in the art in view of this disclosure.

The appended claims set forth novel and inventive aspects of the subject matter disclosed and described above, but the claims may also encompass additional subject matter not specifically recited in detail. For example, certain features, elements, or aspects may be omitted from the disclosure and claims, if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention, as defined by the appended claims.

What is claimed is:

1. An apparatus for filling a wound, the apparatus comprising:
    an array of interconnected polymeric ovules having a truncated ellipsoidal shape, wherein:
        each set of four interconnected ovules defines a fluid pathway extending perpendicularly through the array;
        each truncated ellipsoidal shape comprises an approximately elliptical contact surface at each contact surface between two interconnected ovules; and
        each interconnected polymeric ovule has its longest principal axis oriented substantially perpendicular to the array.

2. The apparatus of claim 1, wherein the array comprises:
    at least three columns comprising two edge columns and at least one central column; and
    at least three rows comprising two edge rows and at least one central row, and
    wherein each set of four interconnected ovules is arranged in two of the at least three rows and two of the at least three columns.

3. The apparatus of claim 1, wherein the array comprises four corner ovules, at least four edge ovules, at least one central ovule, and at least four fluid pathways interstitially therebetween, each central ovule having a truncated ellipsoidal shape with four elliptical contact surfaces, each edge ovule having a truncated ellipsoidal shape with three elliptical contact surfaces, and each corner ovule having a truncated ellipsoidal shape with two elliptical contact surfaces.

4. The apparatus of claim 1, wherein the interconnected ovules are comprised of a polyolefin, a polyester, a polyamide, a polystyrene, a polydiolefin, a polyacrylonitrile, a polysiloxane, or a copolymer or combination thereof.

5. The apparatus of claim 1, wherein each interconnected ovule has its two principal axes other than the longest principal axis, respectively, oriented at approximately a 45° angle to a row direction of the array and at approximately a 45° angle to a column direction of the array.

6. The apparatus of claim 1, wherein each of the interconnected ovules are truncated only at one end of the longest principal axis and at each surface where the ovules are interconnected.

7. The apparatus of claim 1, wherein the array of interconnected ellipsoids or interconnected ovules has an upper surface and a lower surface, and wherein the upper surface or the lower surface or both has a hardness from about 0 Shore A to about 25 Shore A.

8. The apparatus of claim 7, wherein the upper surface or the lower surface or both has a coating disposed thereon that exhibits a hardness of at least 55 Shore A.

9. The apparatus of claim 8, wherein the coating is comprised of a cellulosic material, a polyester, a polyamide, a polycarbonate, a perhalogenated polyolefin, an aramid, a polybenzimidazole, a polysulfone, or a copolymer, combination, or cross-linked gel thereof.

10. The apparatus of claim 1, wherein at least a portion of the interconnected ellipsoids or at least a portion of the interconnected ovules comprise one or more grooves on an outer surface of each ellipsoid or of each ovule that extend at least partially in a direction of its longest principal axis.

11. The apparatus of claim 10, wherein each groove has an average depth no more than 30% of a diameter of each interconnected ovule or of each interconnected ellipsoid along a principal axis direction other than the longest principal axis.

12. The apparatus of claim 1, wherein a longest principal axis of each interconnected ellipsoid or each interconnected ovule is from about 3 mm to about 6 mm.

13. The apparatus of claim 12, wherein each principal axis other than the longest principal axis of each interconnected ellipsoid or each interconnected ovule is from about 2 mm to about 4 mm.

14. The apparatus of claim 1, wherein each fluid pathway has a minimum width dimension from about 500 microns to about 1500 microns.

15. The apparatus of claim 1, wherein the apparatus is translucent.

16. The apparatus of claim 1, further comprising a wound healing agent in or on the array, the wound healing agent comprising a non-steroidal anti-inflammatory drug, a steroid, an anti-inflammatory cytokine, an anaesthetic, an antiseptic, an antimicrobial agent, a growth factor, a peptide, a microRNA, an antioxidant, or a combination thereof.

17. The apparatus of claim 16, wherein the antimicrobial agent comprises silver, a silver salt, a tetracycline, a beta-lactam, a macrolide, an aminoglycoside, a fluoroquinolone, a cellulose ethyl sulfonate, or a combination thereof.

* * * * *